(12) United States Patent
Riemhofer et al.

(10) Patent No.: US 11,253,243 B2
(45) Date of Patent: Feb. 22, 2022

(54) TISSUE RETRACTION SYSTEM

(71) Applicant: NuVasive, Inc., San Diego, CA (US)

(72) Inventors: Byron Riemhofer, San Diego, CA (US); Andrew Morris, San Diego, CA (US); Steven Lillig, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 11 days.

(21) Appl. No.: 16/905,907

(22) Filed: Jun. 18, 2020

(65) Prior Publication Data

US 2021/0007727 A1 Jan. 14, 2021

Related U.S. Application Data

(60) Provisional application No. 62/863,228, filed on Jun. 18, 2019.

(51) Int. Cl.
*A61B 17/02* (2006.01)
*A61B 34/10* (2016.01)
*A61B 90/00* (2016.01)

(52) U.S. Cl.
CPC ...... *A61B 17/0206* (2013.01); *A61B 17/0218* (2013.01); *A61B 34/10* (2016.02); *A61B 90/39* (2016.02); *A61B 2034/104* (2016.02); *A61B 2090/3937* (2016.02)

(58) Field of Classification Search
CPC . A61B 17/02; A61B 17/0206; A61B 17/0218; A61B 34/10; A61B 90/00; A61B 90/39
See application file for complete search history.

(56) References Cited

U.S. PATENT DOCUMENTS

| 7,079,883 | B2 | 7/2006 | Marino et al. |
| 7,582,058 | B1 | 9/2009 | Miles et al. |
| 7,691,057 | B2 | 4/2010 | Miles et al. |
| 7,819,801 | B2 | 10/2010 | Miles et al. |

(Continued)

FOREIGN PATENT DOCUMENTS

| CN | 108175459 | | 6/2018 |
| EP | 2750611 | B1 | 11/2016 |

OTHER PUBLICATIONS

International Search Report for PCT/US2020/038562, ISA/EP, dated Dec. 24, 2020, 6 pages.

(Continued)

*Primary Examiner* — Christopher J Beccia

(57) ABSTRACT

A tissue retraction system comprising a drive gear coupled to a shaft. The tissue retraction system includes a first plurality of linking members located along a second axis and configured to rotate along the second axis based on contact with the drive gear as the drive gear is rotated. The tissue retraction system includes a linking member selector configured to rotate along the first axis, wherein the linking member selector comprises a cylindrical body integrally formed with a handle. The tissue retraction system includes a right arm assembly, a left arm assembly, and a center arm that are each configured to move along trajectories. The tissue retraction system includes a first retractor blade, a second rector blade, and a third retractor blade. The tissue retraction system includes an array with tracking markers.

20 Claims, 19 Drawing Sheets

(56) References Cited

U.S. PATENT DOCUMENTS

| | | |
|---|---|---|
| 8,016,767 B2 | 9/2011 | Miles |
| 8,137,284 B2 | 3/2012 | Miles et al. |
| 8,303,515 B2 | 11/2012 | Miles |
| 8,727,975 B1 | 5/2014 | Pfabe |
| 9,044,280 B1 | 6/2015 | Arambula |
| 9,138,217 B2 | 9/2015 | Smith |
| 9,486,133 B2 | 11/2016 | Lee et al. |
| 9,622,732 B2 | 4/2017 | Martinelli |
| 9,795,367 B1 | 10/2017 | Lee |
| 10,039,539 B2 | 8/2018 | Friedrich |
| 10,709,434 B2 | 7/2020 | Friedrich |
| 2005/0288677 A1 | 12/2005 | Stauber |
| 2007/0282171 A1 | 12/2007 | Karpowicz et al. |
| 2008/0114208 A1 | 5/2008 | Hutton |
| 2011/0224497 A1 | 9/2011 | Weiman et al. |
| 2012/0046527 A1 | 2/2012 | Cianfrani et al. |
| 2012/0323080 A1 | 12/2012 | Deridder |
| 2013/0046147 A1 | 2/2013 | Nichter |
| 2013/0103103 A1 | 4/2013 | Mire |
| 2013/0190575 A1* | 7/2013 | Mast ................. A61B 17/7079 600/215 |
| 2013/0327181 A1 | 12/2013 | Shigematsu |
| 2014/0066719 A1 | 3/2014 | Nichter |
| 2014/0148652 A1 | 5/2014 | Weiman |
| 2014/0350347 A1 | 11/2014 | Karpowicz |
| 2015/0018628 A1 | 1/2015 | Friedrich |
| 2015/0045626 A1 | 2/2015 | Reimels |
| 2015/0230787 A1 | 8/2015 | Friedrich |
| 2015/0265265 A1 | 9/2015 | Hynes |
| 2015/0265320 A1 | 9/2015 | Hynes et al. |
| 2016/0192922 A1 | 7/2016 | Friedrich |
| 2016/0345951 A1 | 12/2016 | Reimels |
| 2016/0361052 A1 | 12/2016 | Reimels |
| 2017/0014118 A1 | 1/2017 | Capote |
| 2017/0014119 A1 | 1/2017 | Capote |
| 2017/0049428 A1 | 2/2017 | Cryder |
| 2017/0150956 A1* | 6/2017 | Baudouin .......... A61B 17/0218 |
| 2018/0177499 A1* | 6/2018 | Sauer ................. A61B 17/0218 |
| 2018/0249992 A1 | 9/2018 | Truckey |
| 2019/0321022 A1 | 10/2019 | Karpowicz |
| 2020/0340558 A1 | 10/2020 | Riemhofer |

OTHER PUBLICATIONS

Written Opinion of the International Search Authority for PCT/US2020/038562, ISA/EP, dated Dec. 24, 2020, 12 pages.

ISA, International Search Report, PCT/US2020/029746 (dated Aug. 20, 2020).

* cited by examiner

TISSUE RETRACTION SYSTEM

FIELD

This disclosure describes a tissue retraction system for use during a surgical procedure.

BACKGROUND

A noteworthy trend in the medical community is the move away from performing surgery via traditional "open" techniques in favor of minimally invasive or minimal access techniques. Open surgical techniques are less desirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements.

Currently available access systems require multiple inputs to actuate components in multiple directions or shifting the anchor point of the retractor from one position to another to create a customized exposure to the target surgical site. There exists a need for an access system that enables a surgeon to create a reproducible, customized exposure to the target surgical site in a faster and less complicated manner.

SUMMARY

In one embodiment, a tissue retraction system includes a drive gear coupled to a shaft. The drive gear is configured to rotate along a first axis based on movement of the shaft. The tissue retraction system also includes a first plurality of linking members located along a second axis and configured to rotate along the second axis based on contact with the drive gear as the drive gear is rotated. The tissue retraction system a second plurality of linking members located along a third axis and configured to rotate along the third axis based on contact with the drive gear as the drive gear is rotated. The tissue retraction system also includes a linking member selector configured to rotate along the first axis. The linking member selector includes a cylindrical body integrally formed with a handle. The cylindrical body includes at least a first protrusion configured to exert a first force on at least one linking member of the first plurality of linking members based on selection, via the handle of the linking member selector, of a position corresponding to the at least one linking member of the first plurality of linking members. The cylindrical body includes at least a second protrusion configured to exert a second force on at least one linking member of the second plurality of linking members based on selection, via the handle of the linking member selector, of a position corresponding to the at least one linking member of the second plurality of linking members. The tissue retraction system also includes a right arm assembly configured to move along a first trajectory based on a corresponding movement of at least two linking members of the first plurality of linking members. The tissue retraction system also includes a first retractor blade coupled to the right arm assembly. The tissue retraction system also includes a left arm assembly configured to move along a second trajectory based on a corresponding movement of at least another two linking members of the first plurality of linking members. The tissue retraction system also includes a second retractor blade coupled to the left arm assembly. The tissue retraction system also includes a center arm configured to move along a third trajectory based on a corresponding movement of at least two linking members of the second plurality of linking members. The tissue retraction system also includes a third retractor blade coupled to the center arm. The tissue retraction system also includes an array. The array includes tracking makers. The array is releasably secured to the center arm.

In one embodiment, a system includes a surgical retractor. The surgical retractor includes includes a drive gear coupled to a shaft. The drive gear is configured to rotate along a first axis based on movement of the shaft. The surgical retractor also includes a first plurality of linking members located along a second axis and configured to rotate along the second axis based on contact with the drive gear as the drive gear is rotated. The surgical retractor also includes a second plurality of linking members located along a third axis and configured to rotate along the third axis based on contact with the drive gear as the drive gear is rotated. The surgical retractor also includes a linking member selector configured to rotate along the first axis. The linking member selector includes a cylindrical body integrally formed with a handle. The cylindrical body includes at least a first protrusion configured to exert a first force on at least one linking member of the first plurality of linking members based on selection, via the handle of the linking member selector, of a position corresponding to the at least one linking member of the first plurality of linking members. The cylindrical body includes at least a second protrusion configured to exert a second force on at least one linking member of the second plurality of linking members based on selection, via the handle of the linking member selector, of a position corresponding to the at least one linking member of the second plurality of linking members. The surgical retractor also includes a right arm assembly configured to move along a first trajectory based on a corresponding movement of at least two linking members of the first plurality of linking members. The surgical retractor also includes a first retractor blade coupled to the right arm assembly. The surgical retractor also includes a left arm assembly configured to move along a second trajectory based on a corresponding movement of at least another two linking members of the first plurality of linking members. The surgical retractor also includes a second retractor blade coupled to the left arm assembly. The surgical retractor also includes a center arm configured to move along a third trajectory based on a corresponding movement of at least two linking members of the second plurality of linking members. The surgical retractor also includes a third retractor blade coupled to the center arm. The surgical retractor also includes an array. The array includes tracking makers. The array is releasably secured to the center arm. The system also includes at least one camera configured to track the array and transmit one or more images of the array to a computing system including a processor. The computing system is configured to display a simulation of the surgical retractor on a display screen.

In one embodiment, the system includes a surgical retractor. The surgical retractor includes a drive gear coupled to a shaft. The drive gear is configured to rotate along a first axis based on movement of the shaft. The surgical retractor also includes a first plurality of linking members located along a second axis and configured to rotate along the second axis based on contact with the drive gear as the drive gear is rotated. The surgical retractor also includes a second plurality of linking members located along a third axis and configured to rotate along the second axis based on contact with the drive gear as the drive gear is rotated. The surgical retractor also includes a linking member selector configured to rotate along the first axis, the linking member selector comprising a cylindrical body integrally formed with the handle, wherein the cylindrical body includes at least a first protrusion configured to exert a first force on at least one linking member of the first plurality of linking members based on selection, via a handle of the linking member selector, of a position corresponding to the at least one linking member of the first plurality of linking members. The first force on the at least one linking member causes a coupling between the at least one linking member of the first plurality of linking members and another linking member of the first plurality of linking members. The cylindrical body includes at least a second protrusion configured to exert a second force on at least one linking member of the second plurality of linking members based on selection, via a handle of the linking member selector, of a position corresponding to the at least one linking member of the second plurality of linking members. The second force on the at least one linking member causes a coupling between the at least one linking member of the second plurality of linking members and another linking member of the second plurality of linking members. The surgical retractor also includes a right arm assembly configured to move along either a first trajectory or a second trajectory. The first trajectory corresponds to a movement of at least two linking members of the first plurality of linking members. The second trajectory corresponds to a movement of at least two linking members of the second plurality of linking members. The surgical retractor also includes a first retractor blade coupled to the right arm assembly. The surgical retractor also includes a left arm assembly configured to move along either the second trajectory or a third trajectory. The third trajectory corresponds to a movement of at least two other linking members of the first plurality of linking members. The surgical retractor also includes a second retractor blade coupled to the left arm assembly. The surgical retractor also includes a center arm configured to move along a fourth trajectory based on a corresponding movement of at least two other linking members of the second plurality of linking members. The surgical retractor also includes a third retractor blade coupled to the center arm. The surgical retractor also includes a post located along a fourth axis parallel and offset to the first axis. The surgical retractor also includes locking teeth secured to the system at a first end of the post, wherein the post includes at least one tapered surface. The surgical retractor also includes an articulating arm connector. The articulating arm connector includes an aperture, a button with a tapered surface, and locking teeth. The aperture is configured to receive the post. The tapered surface of the button is configured to interface with the at least one tapered surface of the post. The locking teeth of the post are configured to engage with the locking teeth secured to the system. The system also includes at least one camera configured to track the array and transmit one or more images of the array to a computing system including a processor. The computing system is configured to display a simulation of the surgical retractor on a display screen.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
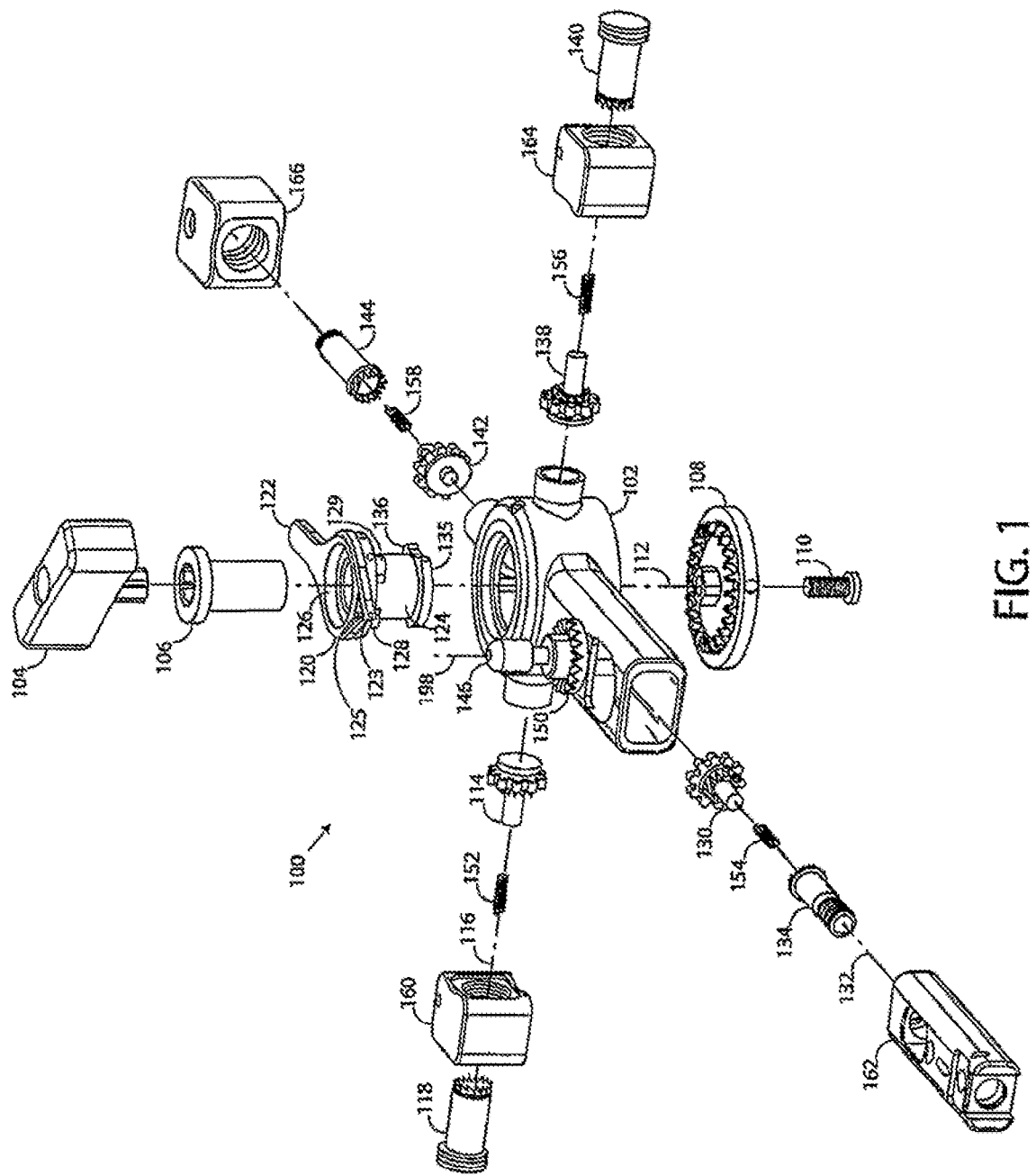
FIG. 1 illustrates an exploded view of an assembly, according to an embodiment of the present disclosure.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention. The surgical access system disclosed herein boasts a variety of inventive features and components that warrant patent protection, both individually and in combination.

The surgical access system according to an exemplary embodiment includes a tissue retractor. The retractor described herein has a plurality of blades configured for insertion through a patient's tissue to a surgical site that can be actuated independently or simultaneously. According to the exemplary embodiment, the plurality of blades may be moved independently or simultaneously in order to create a surgical corridor with a customized size determined by the surgeon user. Further, movement of the plurality of blades is directed by a single input source. In other words, the retractor includes a single input device capable of causing movement of all of the blades, regardless of whether the blades are actuated at the same time or each blade is actuated independently, as opposed to each blade requiring its own input mechanism that only controls movement of that blade.

According to an exemplary embodiment, the capability to actuate the retractor blades independently or simultaneously by a single input source is accomplished by allowing the user to select one of a plurality of different blade actuation modes. For example, the retractor may have at least five blade actuation modes that are activated by positioning a selector in one of five positions. According to the exemplary embodiment, the positions may include a right blade actuation position, a left blade actuation position, a combined right blade and left blade actuation position along a first axis, a combined right blade and left blade actuation along a second axis, and a posterior blade actuation position. In one example, the single input source is configured to rotate along an axis when selecting one of the five positions.

Examples described herein include subsystems that enable a surgical retractor, including an assembly, to be used in a surgical procedure. In one example, the assembly includes a dial that is attachable and detachable to a shaft. In this example, the shaft is coupled to a drive gear. The drive gear is configured to rotate along a first axis of the assembly based on movement of the dial. In this example, the assembly also includes a first linking member that is located along a second axis of the assembly. The first linking member includes a gear and is configured to rotate about the second axis based on contact of the gear with the drive gear as the drive gear is rotated via movement of the dial. By way of example, the gear and the drive gear may be bevel gears. The assembly also includes a second linking member located along the second axis. The second linking member is configured to rotate about the second axis based on rotation of the drive gear and a coupling between the first linking member and the second linking member. In one example, the coupling between the first linking member and the second linking member is based on a mating of a first locking element of the first linking member and a second locking element of the second linking member. In one example, the assembly includes a linking member selector that is configured to rotate about the first axis of the assembly. The linking member selector includes a handle for rotating the linking member selector to a position corresponding to the first linking member. The linking member selector includes a cylindrical body that is integrally formed with the handle. The cylindrical body includes an aperture along a longitudinal axis of the cylindrical body. The cylindrical body also includes a protrusion. The protrusion is configured to exert a force on the first linking member based on selection of the position corresponding to the first linking member. The force on the first linking member causes the coupling between the first linking member and the second linking based on a linear movement of the first linking member along the second axis. The aperture is configured to receive the shaft.

Referring now to the figures, FIG. 1 illustrates an exploded view of an example assembly 100. The assembly 100 comprises a body 102. The body 102 is configured to receive a linking member selector 120 along a first axis 112. The linking member selector 120 is configured to receive a shaft 106 that is coupled to a drive gear 108 via a fastener 110. The shaft 106 is configured to receive a dial 104. The body 102 is configured to receive a first linking member 114 along a second axis 116. The body 102 includes a nut 160 that is configured to receive the first linking member 114 and a second linking member 118 along the second axis 116. The second linking member 118 is configured to receive the first linking member 114. The body 102 is configured to receive a third linking member 130 along a third axis 132. The body 102 is configured to receive a center arm 162. The center arm 162 is configured to receive the third linking member 130 and a fourth linking member 134 along the third axis 132. The fourth linking member 134 is configured to receive the third linking member 130. The body 102 is configured to receive a fifth linking member 138 along the second axis 116. The body 102 includes a nut 164 that is configured to receive the fifth linking member 138 and a sixth linking member 140 along the second axis 116. The sixth linking member 140 is configured to receive the fifth linking member 138. The body 102 is configured to receive a seventh linking member 142 along the third axis 132. The body 102 includes a nut 166 that is configured to receive the seventh linking member 142 and an eighth linking member 144 along the third axis 132. The eighth linking member 144 is configured to receive the seventh linking member 142. The body includes a post 146 along a fourth axis 198. As shown in FIG. 1, the first axis 112 is perpendicular to the second axis 116, and the second axis 116 is perpendicular to the third axis 132. Although these axes are shown to be perpendicular to one another in this example assembly 100, other angles between each of the three axes are envisioned.

The linking member selector 120 comprises a handle 122 for rotating the linking member selector 120 about the first axis 112. The linking member selector 120 comprises a cylindrical body 124 that is integrally formed with the handle 122. The cylindrical body 124 includes an aperture 126 along a longitudinal axis of the cylindrical body 124. The cylindrical body 124 comprises a plurality of protrusions 128, 129, 135, and 136 as shown in FIG. 1, and protrusions 137 and 139 not shown in FIG. 1. The linking member selector 120 comprises a pointer 123 and a window 125 for aligning the linking member selector 120 with a position for selecting at least one linking member and for viewing a marking (not shown) on the body 102 that corresponds with the position. In one example, the pointer 123 is configured to align with a position that selects at least one linking member. In this example, one or more markings (not shown) corresponding to one or more positions for selecting at least one linking member are located along a perimeter of the body 102. Continuing with this example, the one or more markings along the perimeter of the body 102 are visible through the window 125 as the linking member selector 120 is rotated about the first axis 112 to a given position associated with a given marking. In one example, the handle 122 is used to rotate the linking member selector 120 to a position that selects at least one linking member of the linking members 114, 130, 138, and 142. Based on a position selected, at least one of the protrusions of the plurality of protrusions 128, 129, 135, 136, 137, and 139 will exert a force on at least one linking member of the linking members 114, 130, 138, and 142.

For example, based on a desired selection of the first linking member 114, the linking member selector 120 is rotated about the first axis 112 to a given position corresponding to the first linking member 114. As a result of the selection of the first linking member 114, the protrusion 135 will exert a force on the first linking member 114. The force exerted on the first linking member 114 causes the first linking member 114 to move linearly along the second axis 116 from a first position to a second position. In this example, the linear movement of the first linking member 114 from the first position to the second position will result in a coupling between the first linking member 114 and the second linking member 118. In another example, based on rotation of the linking member selector 120 and a selection of the third linking member 130, the protrusion 137 (not shown) will exert a force on the third linking member 130 that causes the third linking member 130 to move linearly along the third axis 132. In this example, the linear movement of the third linking member 130 from a first position to a second position along the third axis 132 will result in a coupling between the third linking member 130 and the fourth linking member 134. In another example, based on rotation of the linking member selector 120 and a selection of the fifth linking member 138, one of the plurality of protrusions 128, 129, 135, 136 and 139 (not shown) will exert a force on the fifth linking member 138 that causes the fifth linking member 138 to move linearly along the second axis 116. In this example, the linear movement of the fifth linking member 138 from a third position to a fourth position along the second axis 116 will result in a coupling between the fifth linking member 138 and the sixth linking member 140. In another example, based on rotation of the linking member selector 120 and a selection of the seventh linking member 142, the protrusion 137 will exert a force on the seventh linking member 142 that causes the seventh linking member 142 to move linearly along the third axis 132. In this example, the linear movement of the seventh linking member 142 from a third position to a fourth position along the third axis 132 will result in a coupling between the seventh linking member 142 and the eighth linking member 144.

As shown in FIG. 1, the aperture 126 of the linking member selector 120 is configured to receive the shaft 106. In one example, the diameter of the aperture 126 and the diameter of the shaft 106 are dimensioned accordingly to allow the shaft 106 to rotate within the aperture 126 and about the first axis 112. In one example, rotation of the shaft 106 is accomplished by movement of the dial 104 when the dial 104 is coupled to the shaft 106. Rotation of the shaft 106 further causes rotation of the drive gear 108 and the linking members 114, 130, 138, and 142.

A spring 152 is interposed between the first linking member 114 and the second linking member 118. A spring 154 is interposed between third linking member 130 and the fourth linking member 134. A spring 156 is interposed between the fifth linking member 138 and the sixth linking member 140. A spring 158 is interposed between the seventh linking member 142 and the eighth linking member 144. In one example, each of the springs 152, 154, 156, and 158 are configured to operate as compression springs. In this example, the springs 152, 154, 156, and 158 are configured to provide a predetermined resistance between the adjacent linking members in order to maintain a distance between the two adjacent linking members that prevents them from coupling with one another. Continuing with this example, the springs 152, 154, 156, and 158 are also configured to compress based on a force exerted by one of the plurality of protrusions 128, 129, 135, 136, 137, and 139 on at least one of the linking members 114, 130, 138, and 142. For example, two adjacent linking members (e.g., first linking member 114 and second linking member 118) are configured to interlock according to predetermined amount of compression on a given spring (e.g., spring 152) according to a force exerted on a given linking member (e.g., linking member 114) as a result of the position of the linking member selector 120.

The nut 160 comprises an internal threaded portion that is configured to engage with a threaded portion of the second linking member 118. In one example, the linking member selector 120 is rotated to a position that corresponds to a selection of the first linking member 114 and thereby causes a coupling between the first linking member 114 and the second linking member 118 as described above. In this example, the dial 104 is rotated in a clockwise direction about the first axis 112 and thereby causes a rotation in a clockwise direction of the drive gear 108 about the first axis 112 and a rotation of the first linking member 114 about the second axis 116. Continuing with this example, as a result of the coupling between the first linking member 114 and the second linking member 118, the second linking member 118 is also rotated about the second axis 116. Based on contact with the internal threaded portion of the nut 160 and the threaded portion of the second linking member 118, the rotational movement of the second linking member 118 is converted to a linear movement of the nut 160 along the second axis 116 and away from the body 102. In this example, as the dial 104 is rotated in a counter-clockwise direction about the first axis 112, the rotational movement of the second linking member 118 is converted to a linear movement of the nut 160 along the second axis 116 and towards the body 102.

The center arm 162 comprises an internal threaded portion that is configured to engage with a threaded portion of the fourth linking member 134. In one example, the linking member selector 120 is rotated to a position that corresponds to selection of the third linking member 130 and thereby causes a coupling between the third linking member 130 and the fourth linking member 134 as described above. In this example, the dial 104 is rotated in a clockwise direction about the first axis 112 and thereby causes a rotation in a clockwise direction of the drive gear 108 about the first axis 112 and a rotation of the third linking member 130 about the third axis 132. Continuing with this example, as a result of the coupling between the third linking member 130 and the fourth linking member 134, the fourth linking member 134 is also rotated about the third axis 132. Based on contact with the internal threaded portion of the center arm 162 and the threaded portion of the fourth linking member 134, the rotational movement of the fourth linking member 134 is converted to a linear movement of the center arm 162 along the third axis 132 and away from the body 102. In this example, as the dial 104 is rotated in a counter-clockwise direction about the first axis 112, the rotational movement of the fourth linking member 134 is converted to a linear movement of the center arm 162 along the third axis 132 and towards the body 102.

The nut 164 comprises an internal threaded portion that is configured to engage with a threaded portion of the sixth linking member 140. In one example, the linking member selector 120 is rotated to a position that corresponds to a selection of the fifth linking member 138 and thereby causes a coupling between the fifth linking member 138 and the sixth linking member 140 as described above. In this example, the dial 104 is rotated in a clockwise direction about the first axis 112 and thereby causes a rotation in a clockwise direction of the drive gear 108 about the first axis 112 and a rotation of the fifth linking member 138 about the second axis 116. Continuing with this example, as a result of the coupling between the fifth linking member 138 and the sixth linking member 140, the sixth linking member 140 is also rotated about the second axis 116. Based on contact with the internal threaded portion of the nut 164 and the threaded portion of the sixth linking member 140, the rotational movement of the sixth linking member 140 is converted to a linear movement of the nut 164 along the second axis 116 and away from the body 102. In this example, as the dial 104 is rotated in a counter-clockwise direction about the first axis 112, the rotational movement of the second linking member 138 is converted to a linear movement of the nut 164 along the second axis 116 and towards the body 102.

The nut 166 comprises an internal threaded portion that is configured to engage with a threaded portion of the eighth linking member 144. In one example, the linking member selector 120 is rotated to a position that corresponds to a selection of the seventh linking member 142 and thereby causes a coupling between the seventh linking member 142 and the eighth linking member 144 as described above. In this example, the dial 104 is rotated in a clockwise direction about the first axis 112 and thereby causes a rotation in a clockwise direction of the drive gear 108 about the first axis 112 and a rotation of the seventh linking member 142 about the third axis 132. Continuing with this example, as a result of the coupling between the seventh linking member 142 and the eighth linking member 144, the eighth linking member 144 is also rotated about the third axis 132. Based on contact with the internal threaded portion of the nut 166 and the threaded portion of the eighth linking member 144, the rotational movement of the eighth linking member 144 is converted to a linear movement of the nut 166 along the third axis 132 and towards the body 102. In this example, as the dial 104 is rotated in a counter-clockwise direction about the first axis 112, the rotational movement of the eighth linking member 144 is converted to a linear movement of the nut 166 along the third axis 132 and away from the body 102.

In one example, the linking member selector 120 is rotated to a position on the body 102 that corresponds to a selection of the first linking member 114 and a selection of the fifth linking member 138. In this example, a first force is exerted on the first linking member 114 by one of the protrusions 128, 129, 135, 136, and 139 and a second force is exerted on the fifth linking member 138 by another one of the protrusions 128, 129, 135, 136, and 139. As described above, the first force causes a coupling between first linking member 114 and the second linking member 118. Also as described above, the second force causes a coupling between the fifth linking member 138 and the sixth linking member 140. Continuing with this example, the dial 104 is rotated in a clockwise direction about the first axis 112 and thereby causes rotation in a clockwise direction of the drive gear 108 about the first axis 112 and a simultaneous rotation of the first linking member 114 and the fifth linking member 138 about the second axis 116. In this example, as a result of the coupling between the first linking member 114 and the second linking member 118 and the coupling between the fifth linking member 138 and the sixth linking member 140, the second linking member 118 and the sixth linking member 140 are also rotated about the second axis 116. Based on contact with the internal threaded portion of the nut 160 and the threaded portion of the second linking member 118 and contact with the internal threaded portion of the nut 164 and the threaded portion of the sixth linking member 140, the rotational movements of the second linking member 118 and the sixth linking member 140 are converted to linear movements of the nut 160 and the nut 164 along the second axis 116 and away from the body 102. In this example, as the dial 104 is rotated in a counter-clockwise direction about the first axis 112, the rotational movements of the second linking member 118 the sixth linking member 140 are converted to linear movements of the nut 160 and the nut 164 along the second axis 116 and towards the body 102.

As shown in FIG. 1, a post 146 is coupled to the body 102. An anti-rotation feature 150 is secured to the body 102 at a first end of the post 146. In one example, the post 146 is configured to attach the assembly 100 to an external arm (not shown) for securing the assembly 100 in a fixed position during a surgical procedure. In one example, the external arm is an articulating arm comprising one or more sections connected by joints that allow each section to bend or turn independently in different directions.

Figure 2:
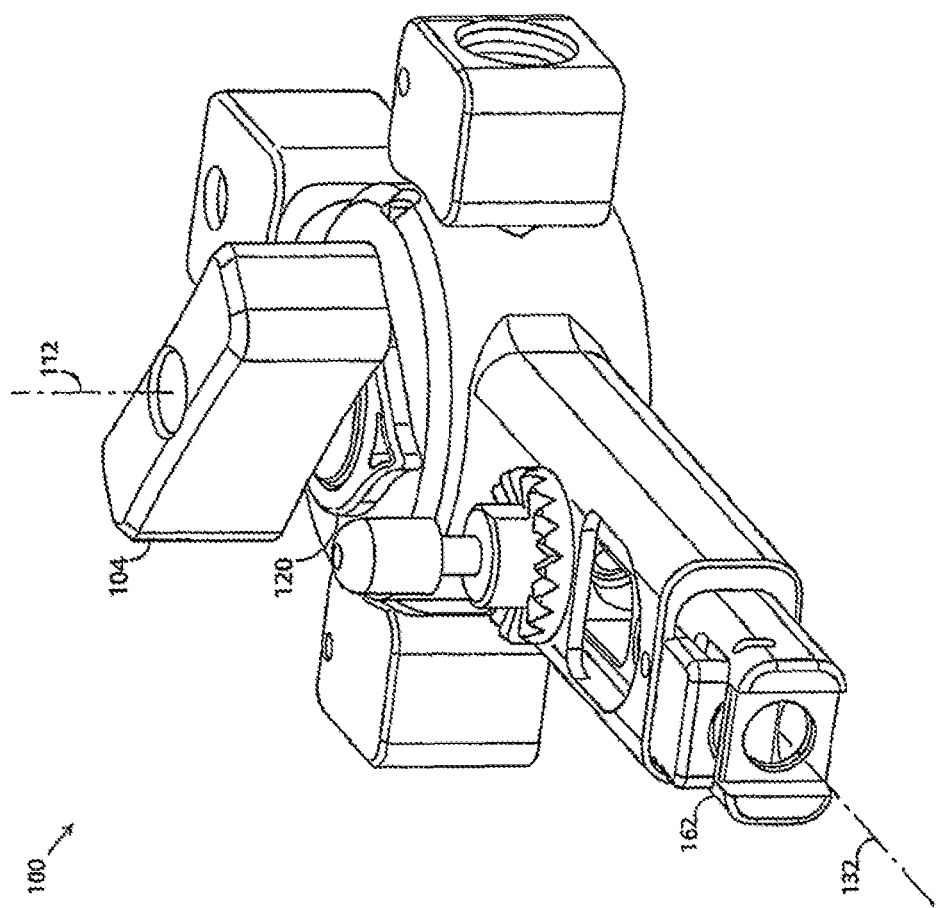
FIG. 2 illustrates another view of the assembly of FIG. 1, according to an embodiment of the present disclosure.

FIG. 2 illustrates an assembled view of the assembly 100 of FIG. 1. As shown in FIG. 2, the linking member selector 120 is in a position corresponding to the seventh linking member 142 (not shown). In this position, based on rotation of the dial 104 about the first axis 112, the rotational movement of the drive gear 108 (not shown) about the first axis 112, the rotational movement of the seventh linking member 142 about the third axis 132, and the rotational movement of the eighth linking member 144 (not shown) about the third axis 132 will be converted to a linear movement of the nut 166 along the third axis 132 as described above.

Figure 3:
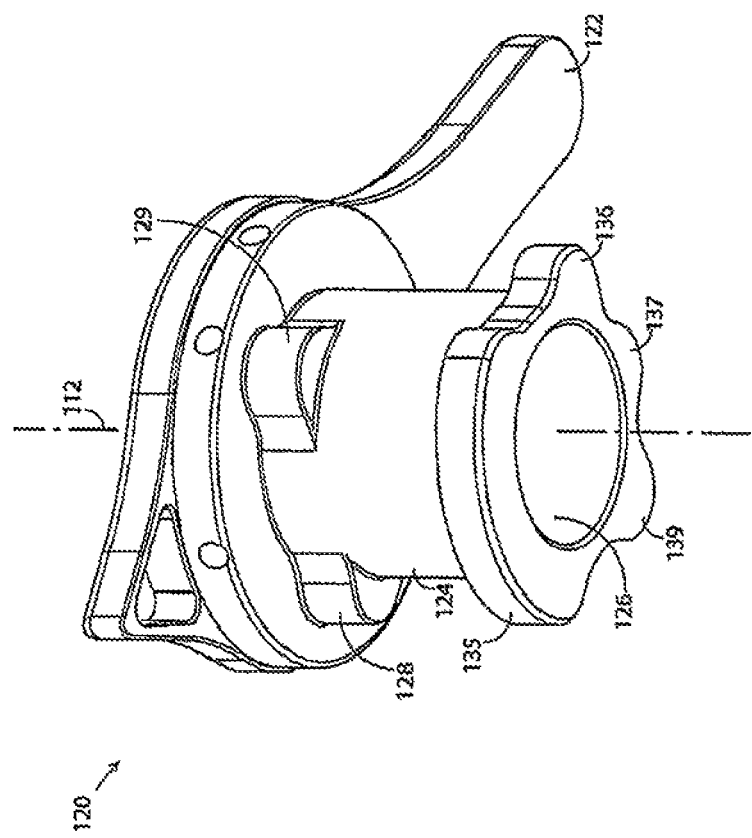
FIG. 3 illustrates a portion of the assembly of FIG. 1, according to an embodiment of the present disclosure.

FIGS. 3 illustrates a view of the linking member selector 120 of FIG. 1. As shown in FIG. 3, the linking member selector 120 comprises a plurality of protrusions 128, 129, 135, 136, 137, and 139 located along the cylindrical body 124. In one example, the protrusion 137 is configured to extend along the entire length of the cylindrical body 124. In this example, a contact position of the third linking member 130 along the first axis 116 and a contact position of the seventh linking member 142 along the first axis 116 are at a position along the first axis 112 that is above the contact positions corresponding to each of the protrusions 135, 136, and 139. The difference between the contact position of the third linking member 130 along the first axis 112 and the contact positions corresponding to each of the protrusions 135, 136, and 139 along the first axis 112 enables only the protrusion 137 to exert a force on the contact position of the third linking member 130. The force exerted on the third liking member 130 results in a coupling between the third linking member 130 and the fourth linking member 134 as described above. Similarly, the difference between the contact position of the seventh linking member 142 along the first axis 112 and the contact position corresponding to each of the protrusions 135, 136, and 139 along the first axis 112 enables only the protrusion 137 to exert a force on the contact position of the seventh linking member 142. The force exerted on the seventh linking member 142 results in a coupling between the seventh linking member 142 and the eighth linking member 144 as described above.

In another example, a contact position of the first linking member 114 along the first axis 112 and a contact position of the fifth linking member 138 along the first axis 112 are at the same position along the first axis 112 as the contact positions corresponding to the protrusions 135, 136, and 139. In this example, the corresponding positions enable only the protrusions 135, 136, and 139 to exert a force on the contact position of the first linking member 114. The force exerted on the first linking member 114 results in a coupling between the first linking member 114 and the second linking member 118 as described above. Similarly, the same position along the first axis 112 of the contact position of the fifth linking member 138 and the contact positions corresponding to the protrusions 135, 136, and 139 enable only the protrusions 135, 136, and 139 to exert a force on the contact position of the fifth linking member 138. The force exerted on the fifth linking member 138 results in a coupling between the fifth linking member 138 and the sixth linking member 140 as described above.

Figure 4:
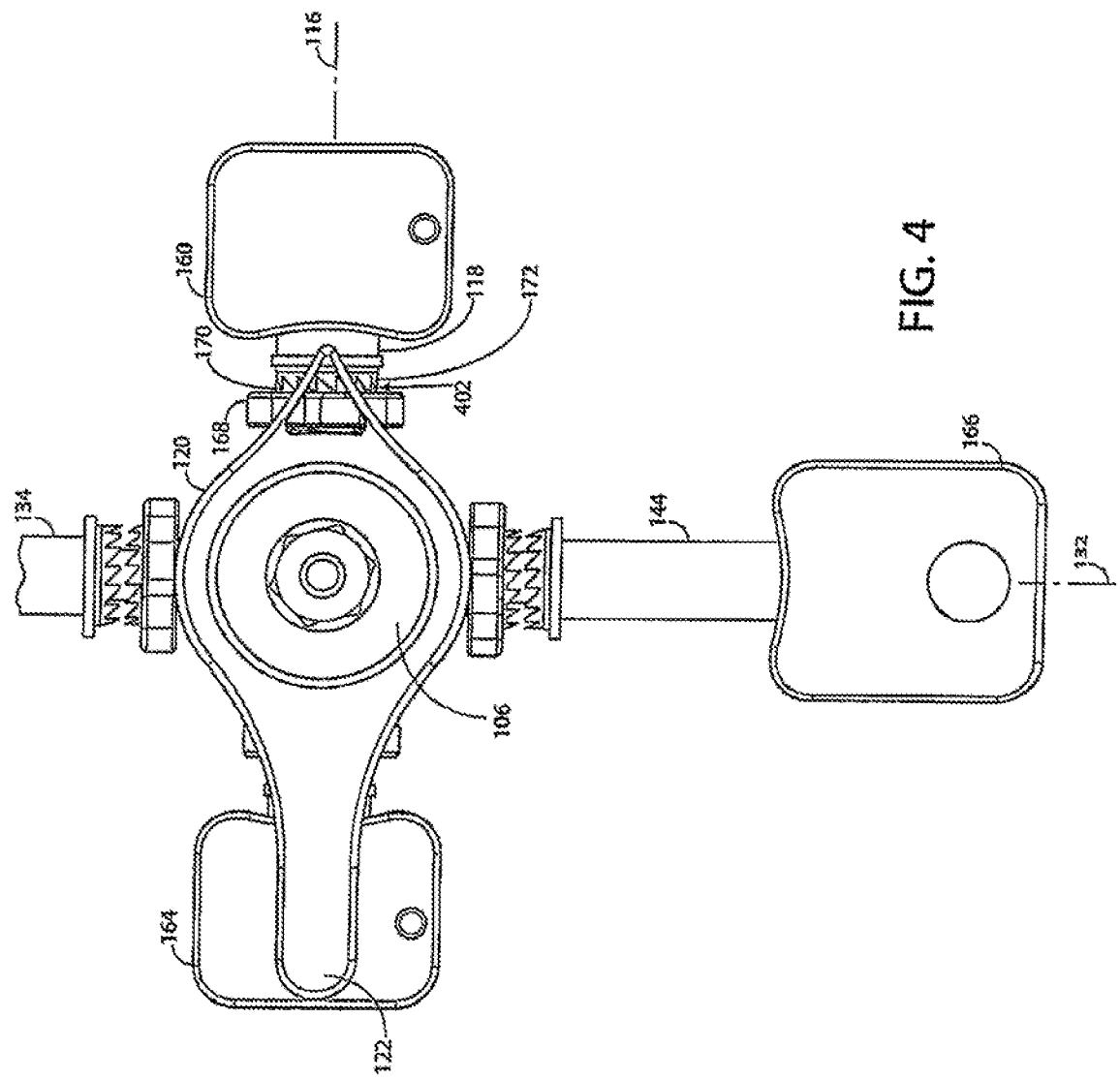
FIG. 4 illustrates a top view of a portion of the assembly of FIG. 1, according to an embodiment of the present disclosure.

FIG. 4 illustrates a top view of a subset of the components of the assembly 100 in FIG. 1. As shown in FIG. 4, the linking member selector 120 has been rotated to a position corresponding to the first linking member 114 (not shown). The first linking member 114 comprises a first gear 168 located along the second axis 116 and configured to rotate based on contact with the drive gear 108 (not shown) of FIG. 1 as the drive gear 108 is rotated. The first linking member 114 includes locking teeth 170 extending from the first gear 168. The second linking member 118 comprises locking teeth 172 extending from the second linking member 118. The locking teeth 172 extending from the second linking member 118 are configured to interlock with the locking teeth 170 extending from the first gear 168 based on a linear movement of the first linking member 118 from a first position along the second axis 116 to a second position along the second axis 116, as shown in FIG. 4. In this scenario, the locking teeth 172 extending from the second linking member 118 are configured to separate from the locking teeth 170 extending from the first gear 168 based on a linear movement of the first linking member 118 from the second position along the second axis 116 to a first position along the second axis 116. In one example, the second linking member 118 comprises a leadscrew configured to translate a rotational movement into a linear movement based on rotation of the drive gear 108 and the coupling between the first linking member 114 and the second linking member 118.

Figure 5:
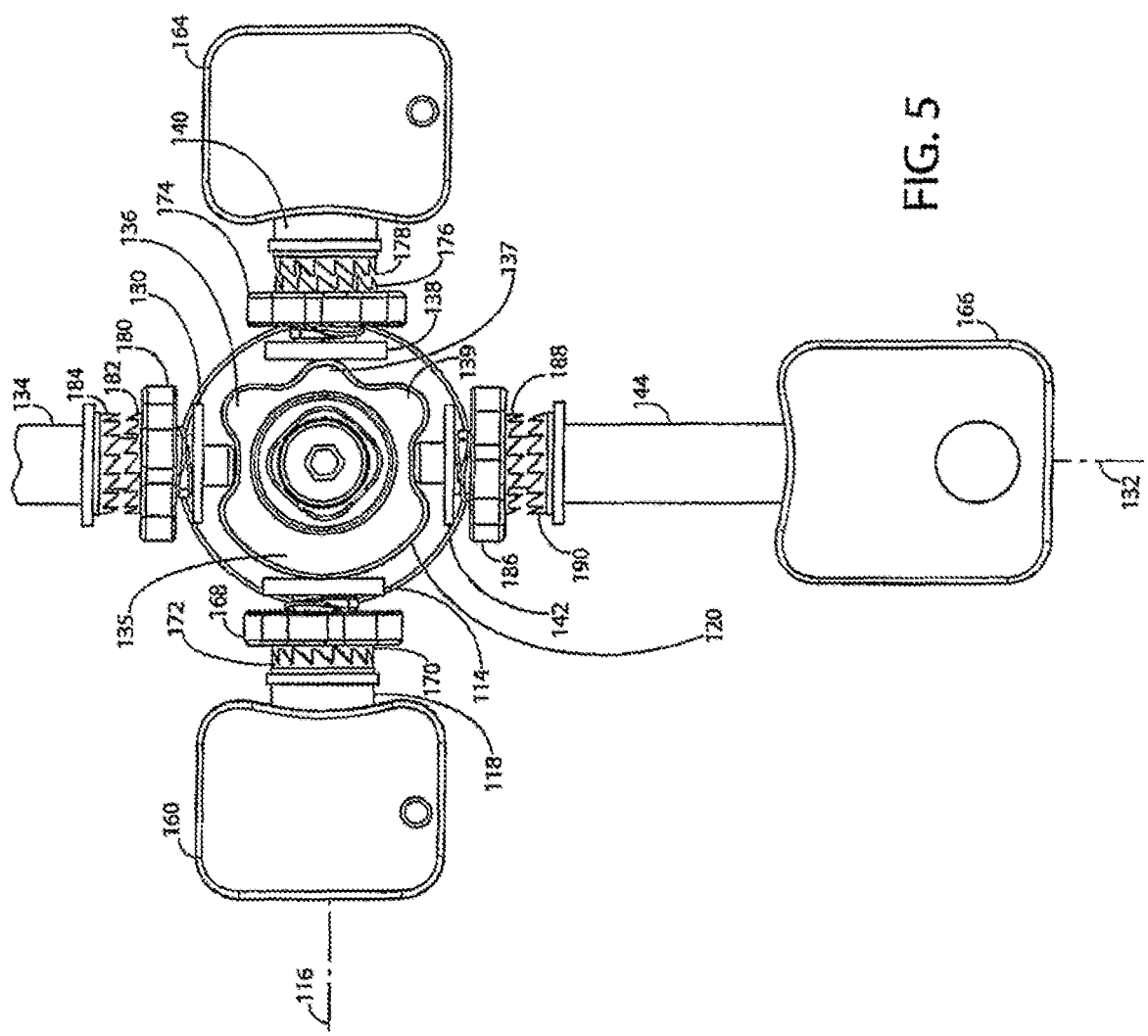
FIG. 5 illustrates a bottom view of a portion of the assembly of FIG. 1, according to an embodiment of the present disclosure.

FIG. 5 illustrates a bottom view that corresponds to the top view of FIG. 4. As shown in FIG. 5, the third linking member 130 comprises a second gear 180 located along the third axis 132 and configured to rotate based on contact with the drive gear 108 (not shown) of FIG. 1 as the drive gear 108 is rotated. The third linking member 130 includes locking teeth 182 extending from the second gear 180. The fourth linking member 134 comprises locking teeth 184. The locking teeth 184 extending from the fourth linking member 134 are configured to interlock with the locking teeth 182 extending from the second gear 180 based on a linear movement of the third linking member 130 from a first position along the third axis 132 to a second position along the third axis 132. The locking teeth 184 extending from the fourth linking member 134 are configured to disengage from the locking teeth 182 extending from the second gear 180 based on a linear movement of the third linking member 130 from the second position along the third axis 132 to the first position along the third axis 132. In one example, the fourth linking member 134 comprises a leadscrew configured to translate a rotational movement into a linear movement based on rotation of the drive gear 108 and the coupling between the third linking member 130 and the fourth linking member 134.

As shown in FIG. 5, the fifth linking member 138 comprises a third gear 174 located along the second axis 116 and configured to rotate based on contact with the drive gear 108 of FIG. 1 as the drive gear 108 is rotated. The fifth linking member 138 includes locking teeth 176 extending from the third gear 174. The sixth linking member 140 also includes locking teeth 178. The locking teeth 178 extending from the sixth linking member 140 are configured to interlock with the locking teeth 176 extending from the third gear based on a linear movement of the fifth linking member 138 from a third position along the second axis 116 to a fourth position, as shown in FIG. 5, along the second axis 116. The locking teeth 176, 178 are configured to disengage based on a linear movement of the fifth linking member 138 from the fourth position along the second axis 116 to the third position along the second axis 116.

As shown in FIG. 5, the seventh linking member 142 comprises a fourth gear 186 located along the third axis 132 and configured to rotate based on contact with the drive gear 108 of FIG. 1 as the drive gear 108 is rotated. The seventh linking member 142 includes locking teeth 188 extending from the fourth gear 186. The eighth linking member 144 also comprises locking teeth 190. The locking teeth 188, 190 are configured to interlock based on a linear movement of the seventh linking member 142 from a third position along the third axis 132 to a fourth position along the third axis 132. The locking teeth 188, 190 are configured to disengage based on a linear movement of the seventh linking member 142 from the fourth position along the third axis 132 to the third position along the third axis 132.

Figure 6:
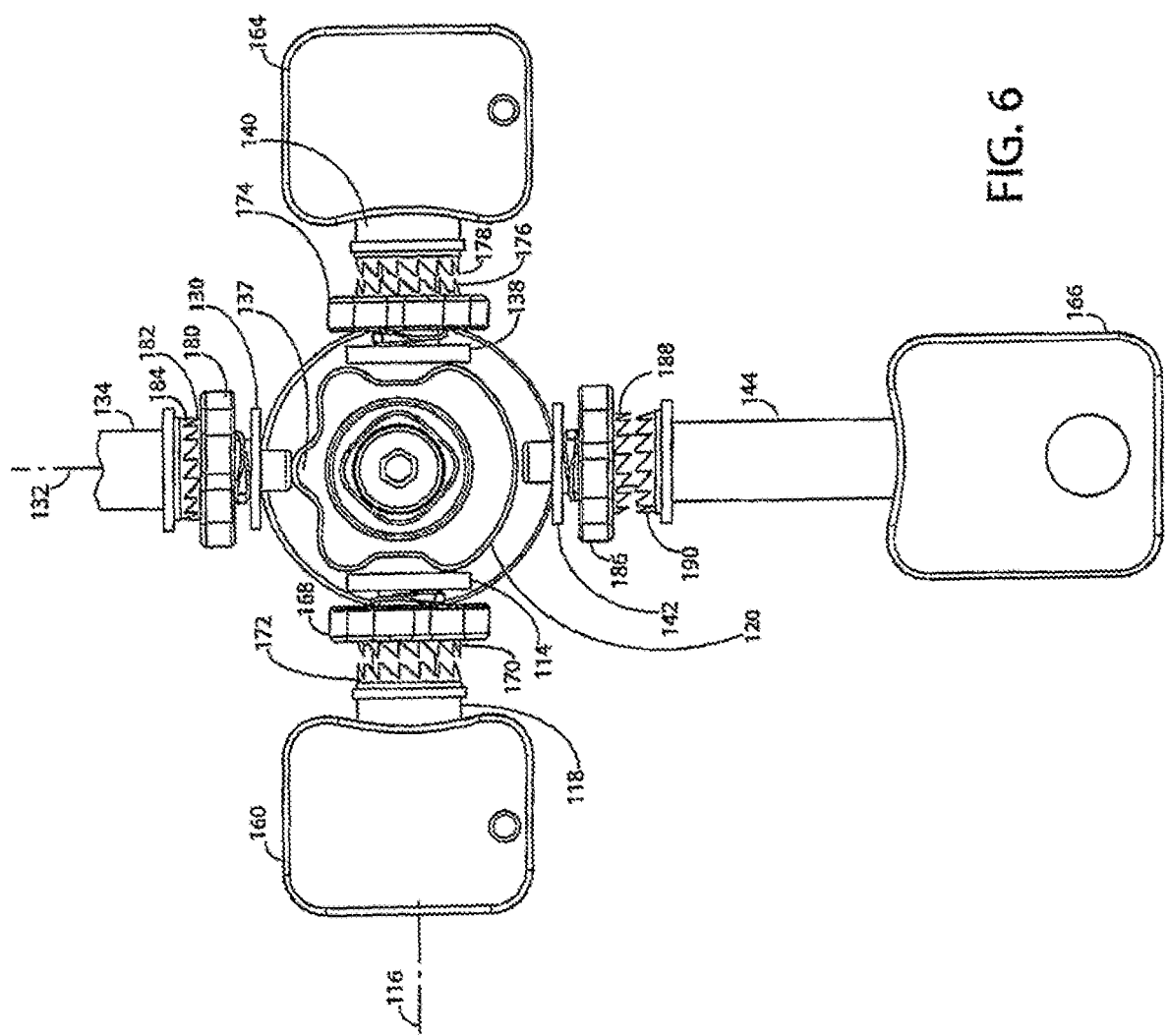
FIG. 6 illustrates a bottom view of a portion of the assembly of FIG. 1, according to an embodiment of the present disclosure.

FIG. 6 illustrates a bottom view of a subset of the components of the assembly 100 in FIGS. 1 and 5. As shown in FIG. 6, the linking member selector 120 has been rotated to a position corresponding to the third linking member 130. In this scenario, the locking teeth 184 extending from the fourth linking member are configured to interlock with the locking teeth 182 extending from the second gear 180 based on a linear movement of the third linking member 130 from a first position along the third axis 132 to a second position, as shown in FIG. 6, along the third axis 132. In this scenario, the locking teeth 182, 184 are configured to disengage based on a linear movement of the third linking member 130 from the second position along the third axis 132 to the first position along the third axis 132.

Figure 7:
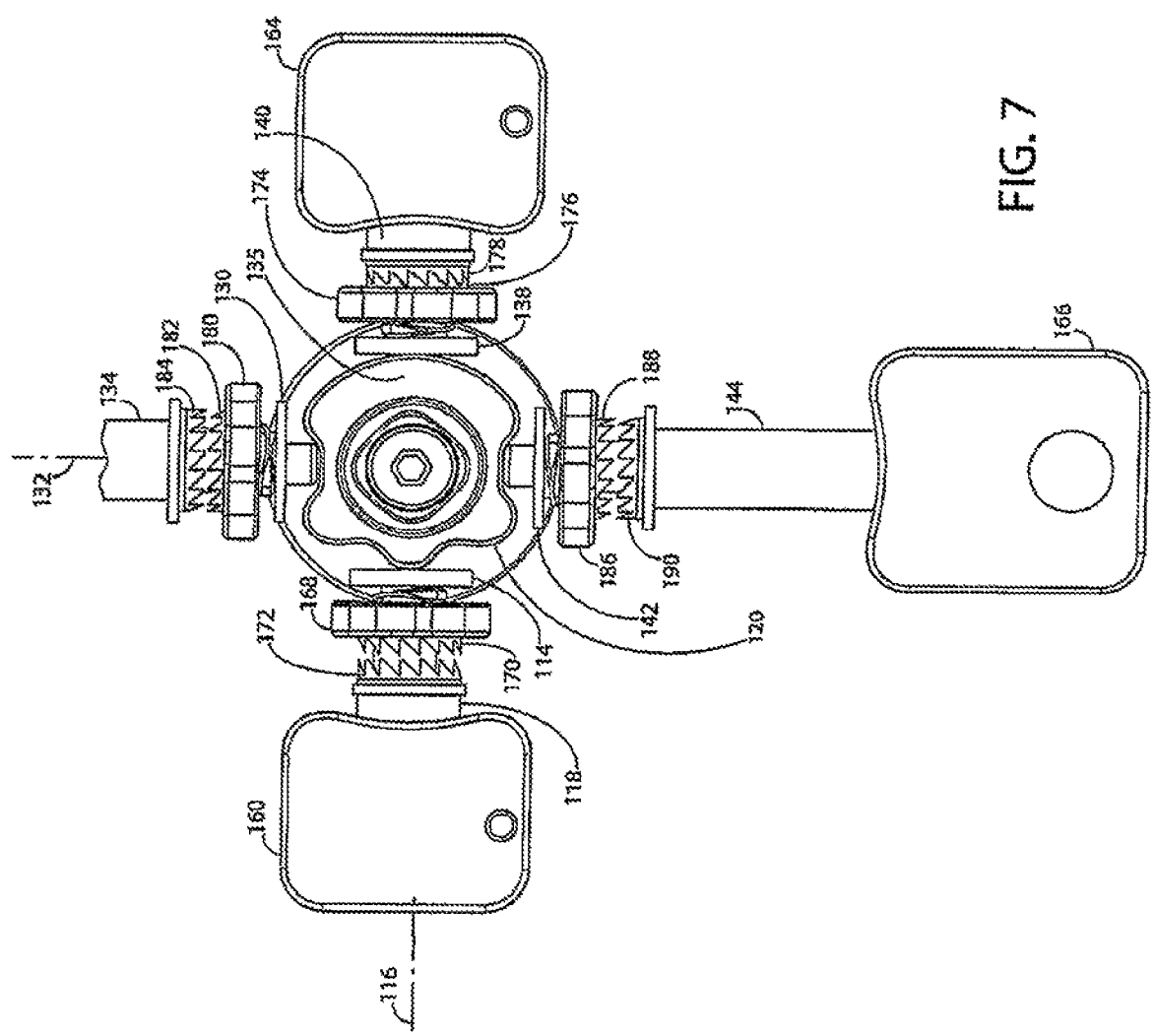
FIG. 7 illustrates a bottom view of a portion of the assembly of FIG. 1, according to an embodiment of the present disclosure.

FIG. 7 illustrates a bottom view of a subset of the components of the assembly 100 in FIGS. 1 and 5. As shown in FIG. 7, the linking member selector 120 has been rotated to a position corresponding to the fifth linking member 138. In this scenario, the locking teeth 176, 178 are configured to interlock based on a linear movement of the fifth linking member 138 from a third position along the second axis 116 to a fourth position, as shown in FIG. 7, along the second axis 116. In this scenario, the locking teeth 176, 178 are configured to disengage based on a linear movement of the fifth linking member 138 from the fourth position along the second axis 116 to a third position along the second axis 116.

Figure 8:
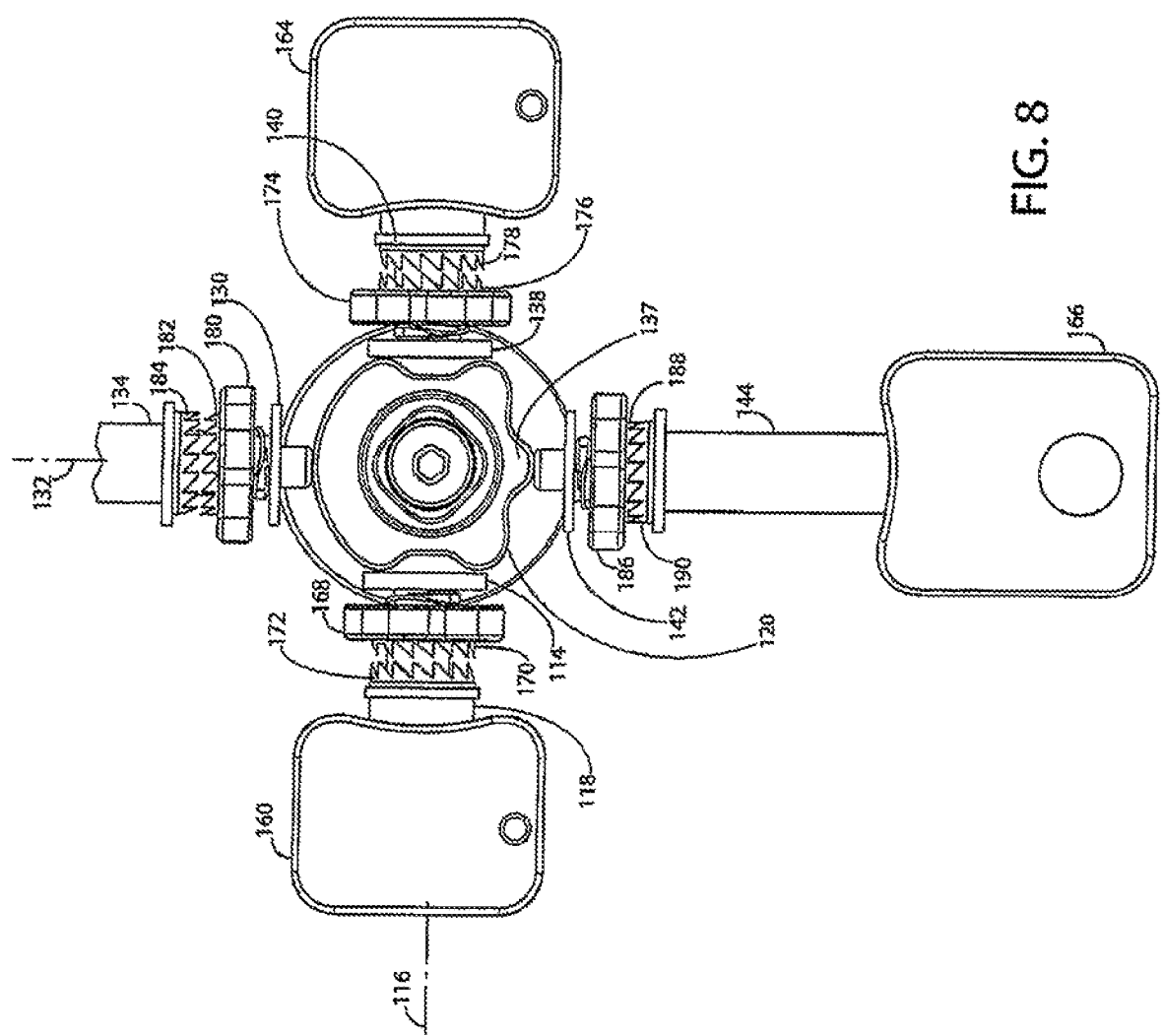
FIG. 8 illustrates a bottom view of a portion of the assembly of FIG. 1, according to an embodiment of the present disclosure.

FIG. 8 illustrates a bottom view of a subset of the components of the assembly 100 in FIGS. 1 and 5. As shown in FIG. 8, the linking member selector 120 has been rotated to a position corresponding to the seventh linking member 142. In this scenario, the locking teeth 190 extending from 144 are configured to interlock with the locking teeth188 extending from the seventh linking member 142 based on a linear movement of the seventh linking member 142 from a third position along the third axis 132 to a fourth position, as shown in FIG. 8, along the third axis 132. In this scenario, the locking teeth 188, 190 are configured to disengage based on a linear movement of the seventh linking member 142 from the fourth position along the third axis 132 to the third position along the third axis 132.

Figure 9:
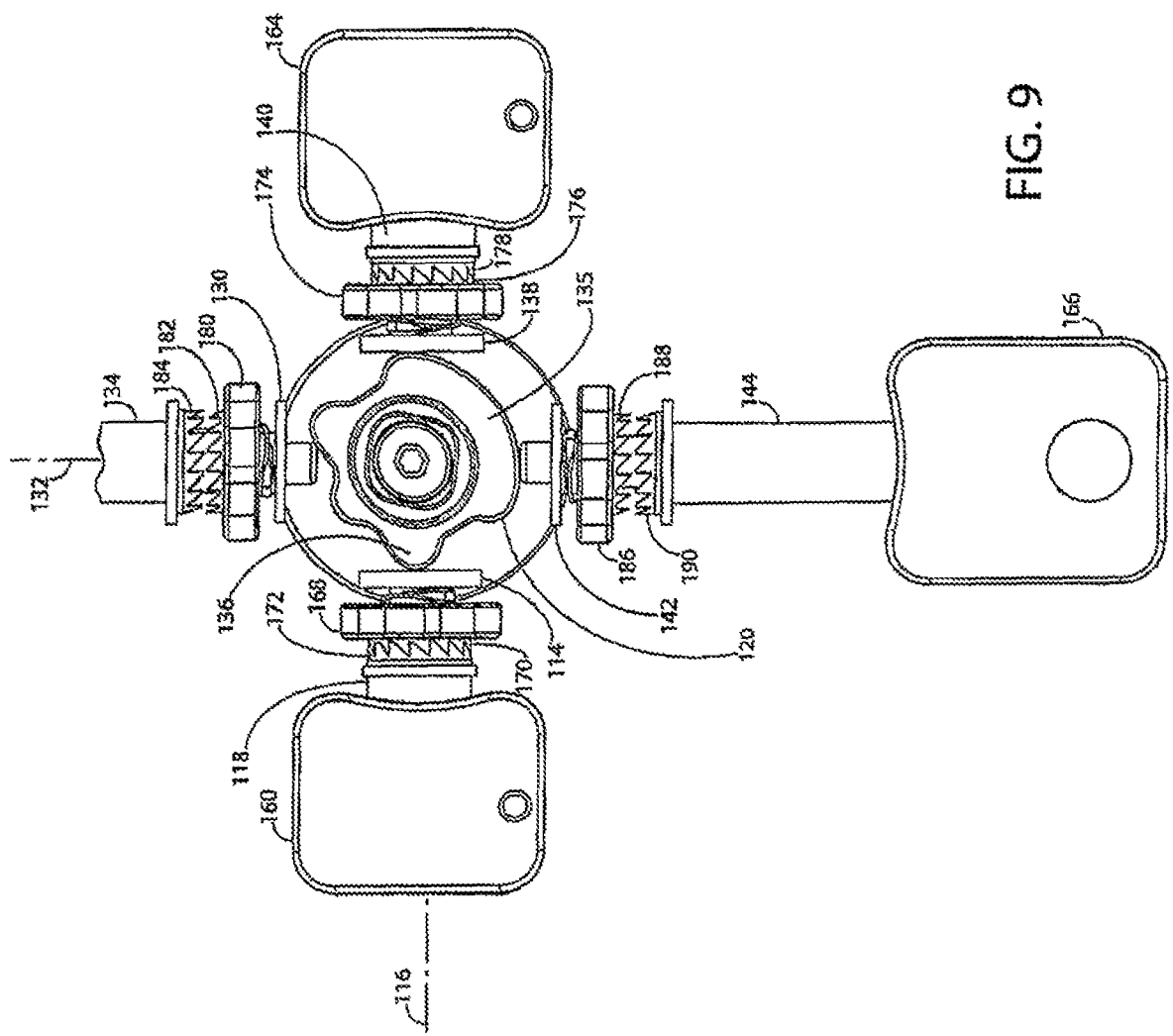
FIG. 9 illustrates a bottom view of a portion of the assembly of FIG. 1, according to an embodiment of the present disclosure.

FIG. 9 illustrates a bottom view of a subset of the components of the assembly 100 in FIGS. 1 and 5. As shown in FIG. 9, the linking member selector 120 has been rotated to a position corresponding to the first linking member 114 and the fifth linking member 138. In this scenario, the locking teeth 172 extending from the second linking member 118 are configured to interlock with or disengage from the locking teeth 170 extending from the first gear 168 as described above. Further, in this scenario, the locking teeth 178 extending from the sixth linking member 140 are configured to interlock with or disengage from with the locking teeth 176 extending from the third gear 174 as described above.

Figure 10:
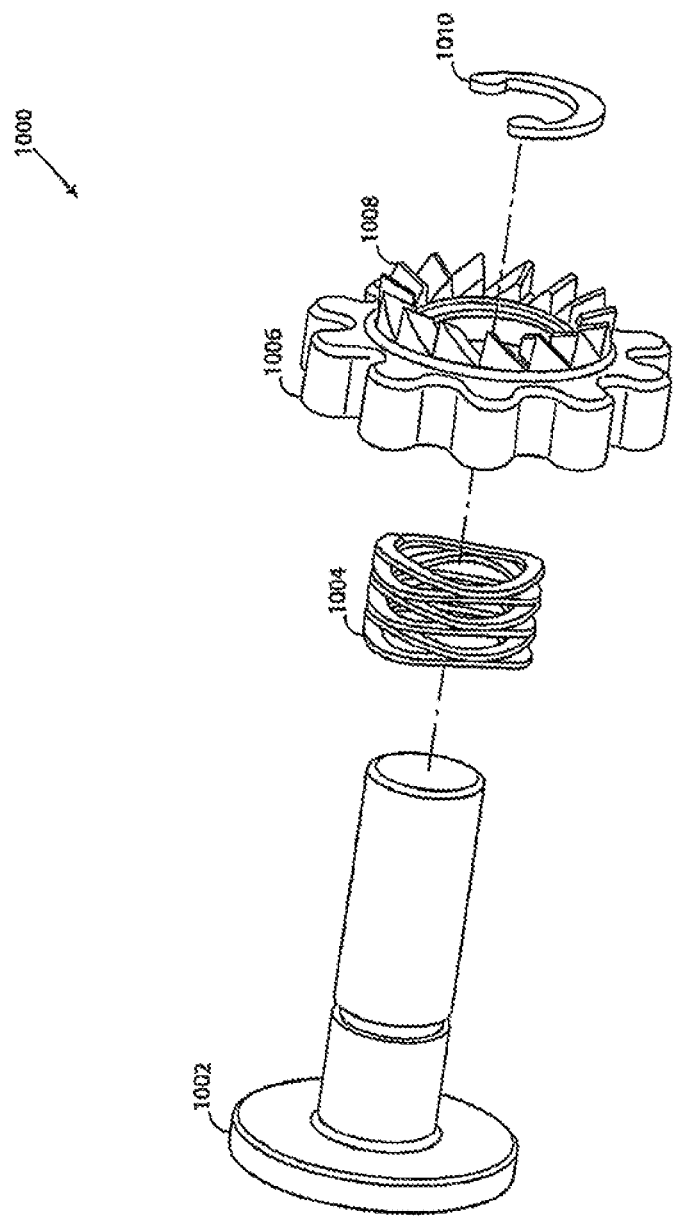
FIG. 10 illustrates an example pinion assembly according to an embodiment of the present disclosure.

FIG. 10 illustrates an example pinion sub-assembly 1000. The pinion sub-assembly 1000 comprises a linking member 1002, a spring 1004, a gear 1006, and a retaining element 1010. The gear 1006 comprises locking teeth 1008. The linking member 1002 is configured to receive the spring 1004, the gear 1006, and the retaining element 1010. The retaining element 1010 is configured to retain the spring 1004 and the gear 1006 from advancing past a given position along the linking member 1002.

In one example, the linking members 114, 130, 138, and 142, as described above, comprise all of the components of the pinion sub-assembly 1000. In this example, the linking member 1002 operates in a similar manner as described with respect to the linking members 114, 130, 138, and 142. Continuing with this example, the gear 1006 and the locking teeth 1008 also operate in a similar manner as described with the first gear 168 and the locking teeth 170, the second gear 180 and the locking teeth 182, the third gear 174 and the locking teeth 176, and the fourth gear 186 and the locking teeth 188, respectively. Further, in this example, the spring 1004 is configured to compress based on a force exerted by a protrusion (e.g., one of the protrusions 128, 129, 135, 136, 137, and 139 of FIG. 3) on the linking member 1002 (e.g., one of the linking members 114, 130, 138, 142 of FIG. 1) and based on a rotational position of the locking teeth 1008 with respect to the locking teeth of another linking member.

In one scenario, referring to FIG. 5, if the tips of the locking teeth 170 and the tips locking teeth 172 are in a given rotational position along the second axis 116 as the first linking member 114 is moved linearly along the first axis 116 towards the second linking member 118, then it is possible that the locking teeth 170 and 172 will be unable to interlock with one another as shown in FIG. 5. Further, it is also possible that the linking member selector 120 could also become temporarily stuck in this position based on the tips of the locking teeth 170 and 172 preventing the locking teeth 170 and 172 from interlocking. In order to overcome this scenario, referring back to FIG. 10, the spring 1004 is compressed as the linking member 1002 is moved along a linear axis towards another linking member while the tips of the locking teeth 1008 encounter the tips of the locking teeth of another linking member at a rotational position that prevents the locking teeth 1008 from interlocking with the locking teeth of another linking member. In this scenario, upon a rotation of the dial 104 and the drive gear 108, the locking teeth 1008 (e.g., the locking teeth 170 of FIG. 5) would rotate about an axis just enough where the tips of the locking teeth 1008 are no longer in direct contact with the tips of the locking teeth corresponding to another linking member. Continuing with this scenario, based on a rotational movement of the linking member 1002, the stored mechanical energy in the spring 1004 would be released and thereby cause the linking member 1002 (e.g., the linking member 114 of FIG. 5) to further move along the linear axis to a given position that enables the locking teeth 1008 (e.g., the locking teeth 170 of FIG. 5) to interlock with the locking teeth (e.g., the locking teeth 172 of FIG. 5) of another linking member (e.g., the linking member 118 of FIG. 5).

Figure 11:
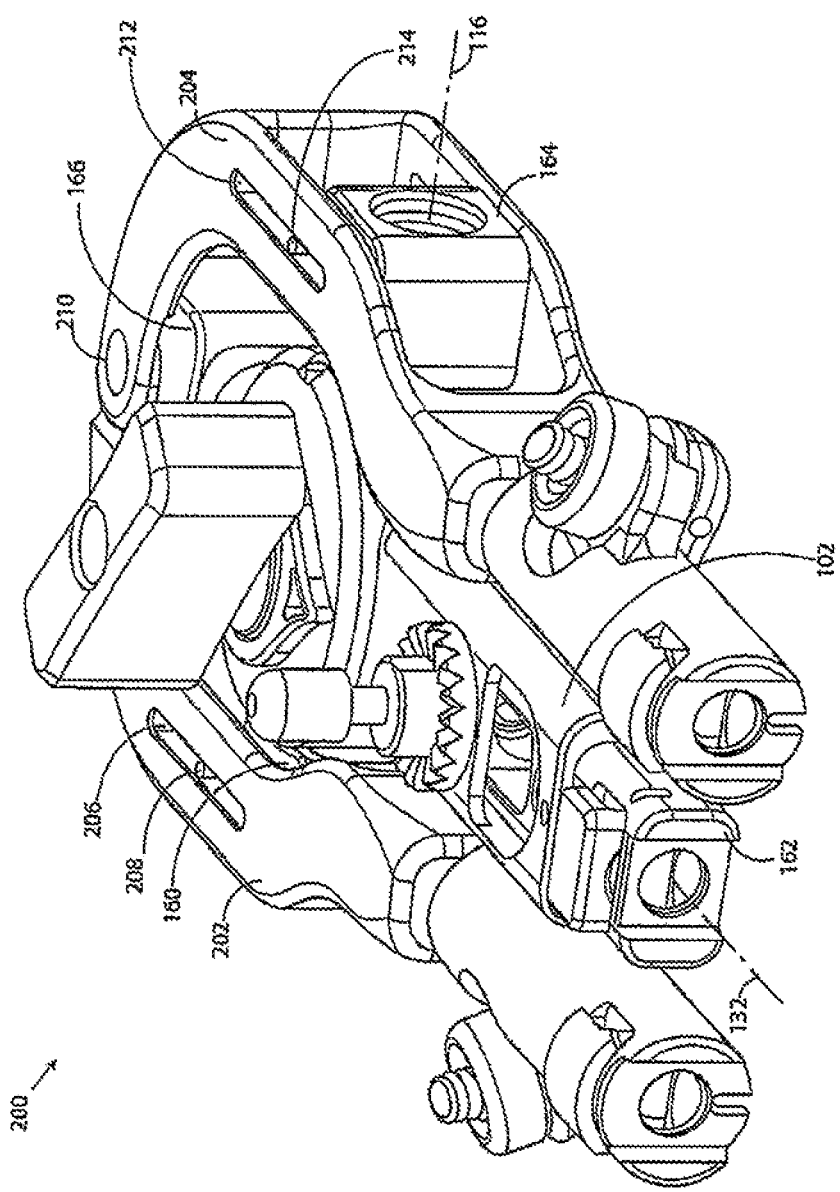
FIG. 11 illustrates an example surgical retractor, according to an embodiment of the present disclosure.

FIG. 11 illustrates an example surgical retractor 200. The surgical retractor 200 comprises the assembly 100 of FIG. 1, a right arm assembly 202, and a left arm assembly 204. As shown in FIG. 11, the right arm assembly 202 comprises a channel 206. The channel 206 is configured to receive a pin 208 that is coupled to the nut 160 of FIG. 1. The right arm assembly 202 comprises an aperture for receiving a pin 210 that is coupled to the nut 166 of FIG. 1. The left arm assembly 204 comprises a channel 212. The channel 212 is configured to receive a pin 214 that is coupled to nut 164 of FIG. 1. The left arm assembly 204 comprises an aperture for also receiving the pin 210 that is coupled to the nut 166 of FIG. 1.

In one example, based on the position of linking member selector 120 corresponding to first linking member 114 (not shown) and rotation of the dial 104 as described above, the nut 160 is configured to move away from or towards the body 102 about the second axis 116. In this example, the right arm assembly 202 is configured to move away from or towards the body 102 based on the force exerted by the pin 208 on the right arm assembly 202 in addition to the right arm assembly 202 being configured to pivot around the pin 210.

In one example, based on the position of linking member selector 120 corresponding to seventh linking member 142 (not shown) and rotation of the dial 104 as described above, the nut 166 is configured to move away from or towards the body 102 about the third axis 132. In this example, the right arm assembly 202 and left arm assembly 204 are configured to move away from or towards the body 102 based on the force exerted by the pin 210 on the right arm assembly 202 and the left arm assembly 204.

In one example, based on the position of linking member selector 120 corresponding to fifth linking member 138 (not shown) and rotation of the dial 104 as described above, the nut 164 is configured to move away from or towards the body 102 along the second axis 116. In this example, the left arm assembly 204 is configured to move away from or towards the body 102 based on the force exerted by the pin 214 on the left arm assembly 204 in addition to the left arm assembly 204 being configured to pivot around the pin 210.

In one example, based on the position of linking member selector 120 corresponding to first linking member 114 and the fifth linking member 138 (not shown) and rotation of the dial 104 as described above, the nut 160 and the nut 164 are configured to move away from or towards the body 102 along the second axis 116. In this example, the right arm assembly 202 and the left arm assembly 204 are configured to move away from or towards the body 102 based on the force exerted by the pin 208 on the right arm assembly 202, the force exerted by the pin 214 on the left arm assembly 204, the right arm assembly 202 being configured to pivot around the pin 210, and the left arm assembly 204 being configured to pivot around the pin 210. In one example, the right arm assembly 202, the left arm assembly 204, and the center arm 162 are each configured to receive a retractor blade for use during a surgical procedure.

Figure 12:
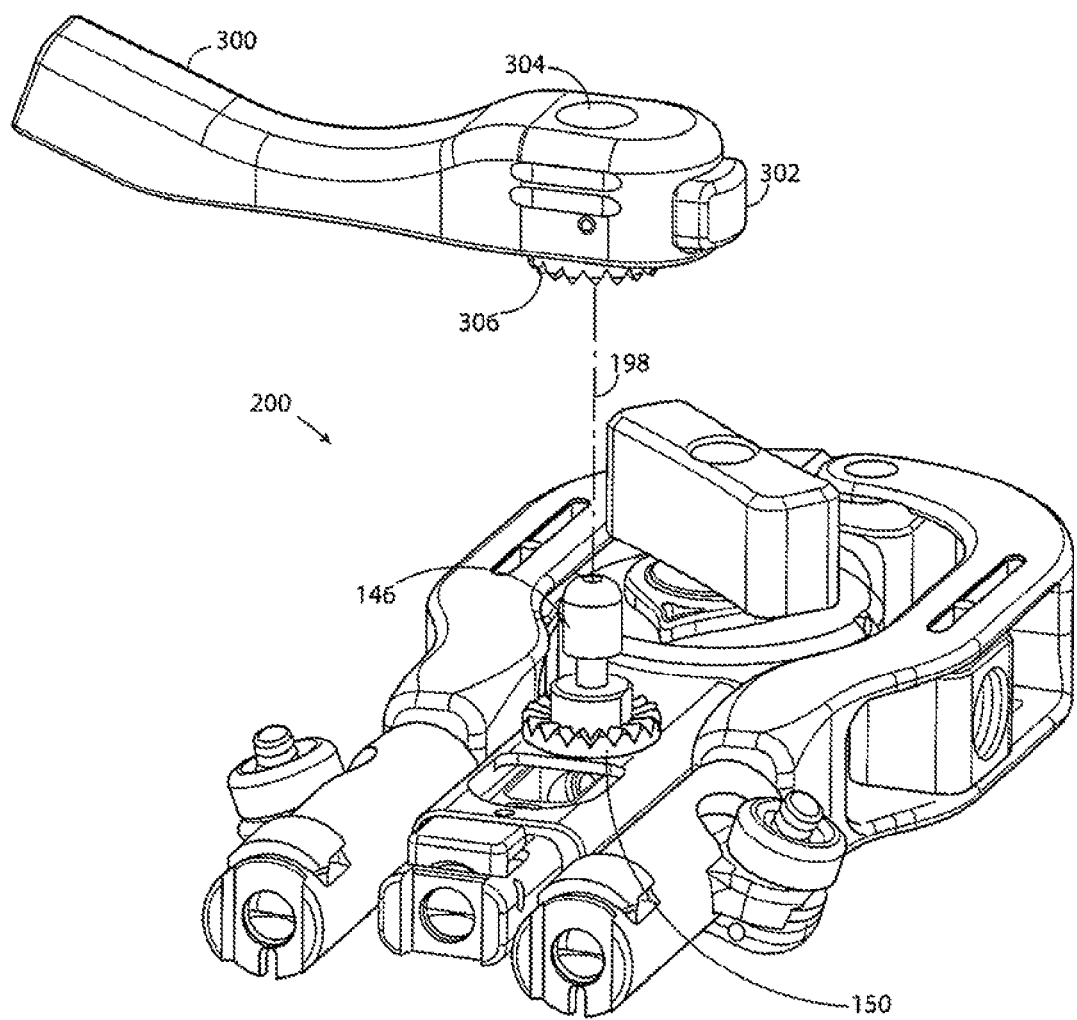
FIG. 12 illustrates an example tissue retraction system, according to an embodiment of the present disclosure.

FIG. 12 illustrates the example surgical retractor 200 and an example articulating arm connector 300. The articulating arm connector 300 comprises a button 302, an aperture 304, and locking teeth 306.

The aperture 304 is configured to receive the post 146 along the fourth axis 198. The locking teeth 306 are configured to interlock with the locking teeth 150. As shown in FIG. 12, the articulating arm connector 300 is configured to attach to a single point of the surgical retractor 200. A single point of attachment to the surgical retractor 200 may reduce the time needed during a surgical procedure.

The button 302 is spring loaded in the engaged state. The button 302 also has a lead in chamfer (not shown) allowing it to depress when aperture 304 receives the post 146. This allows the articulating arm connector 300 to be attached to the surgical retractor 200 without having to press the button. The button 302 has a mating tapered surface that interfaces with the tapered cut of the post 146. That taper pulls the parts together into other tapers and thereby eliminating any movement between the articulating arm connector 306 and the surgical retractor 200. To detach the articulating arm connector 300 from the surgical retractor 200, the button is pressed and the articulating arm connector 300 is separated from the surgical retractor 200. In one example, the articulating arm connector 300 utilizes tapers to reduce play in all three planes (e.g., x, y, and z) fora secure fit.

Figure 13:
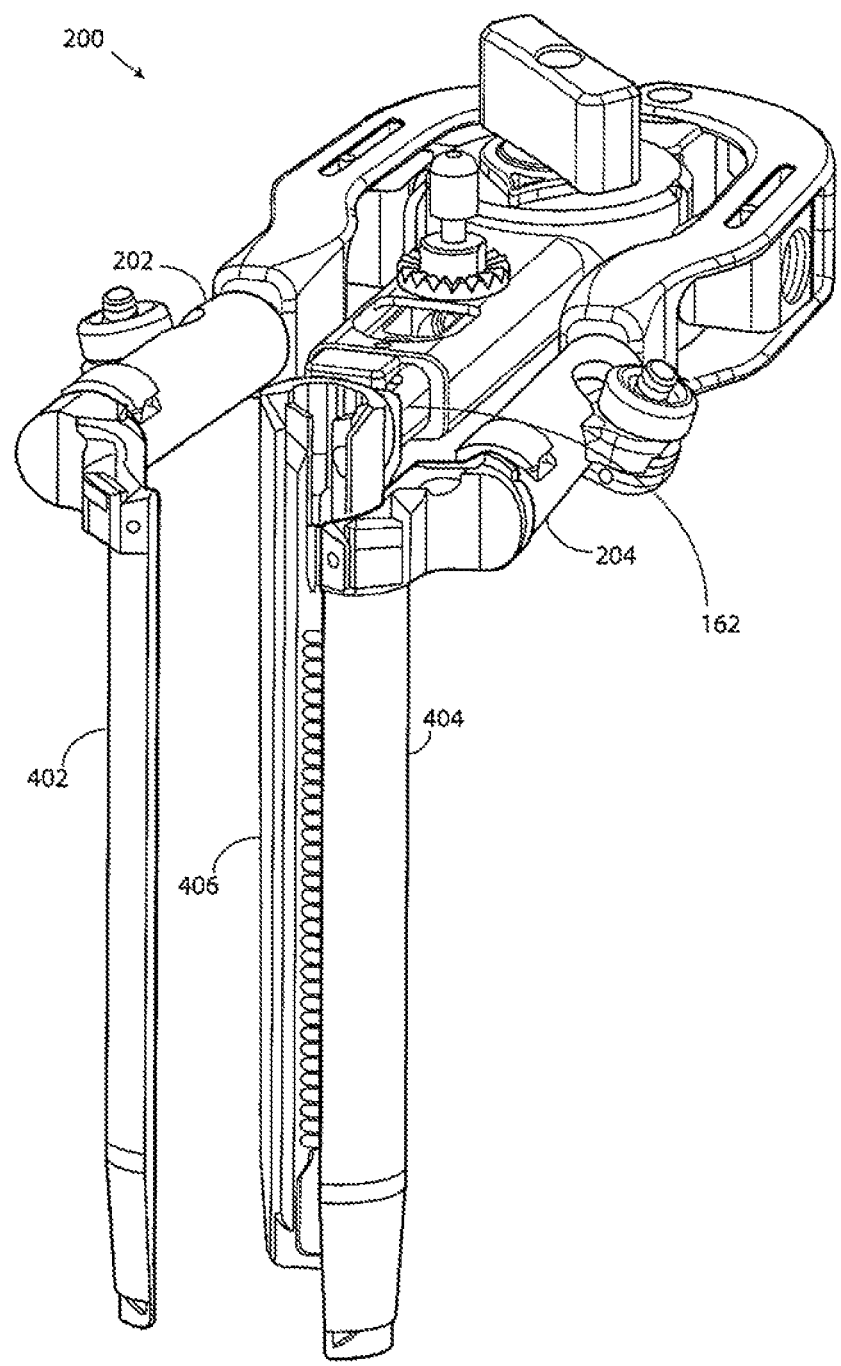
FIG. 13 illustrates an example tissue retraction system, according to an embodiment of the present disclosure.

FIG. 13 illustrates the example surgical retractor 200 with retractor blades 402, 404, and 406 in an open position. As described above, the example surgical retractor 200 comprises the assembly 100 of FIG. 1.

In one embodiment, the surgical retractor 200 includes a first retractor blade 402 coupled to the right arm assembly 202, a second retractor blade 404 coupled to the left arm assembly 204, and third retractor blade 406 coupled to the center arm 162. In one example, the surgical retractor 200 includes a drive gear (e.g., drive gear 108 of FIG. 1) coupled to a shaft (e.g., shaft 106 of FIG. 1). The drive gear is configured to rotate along a first axis (e.g., first axis 112 of FIG. 1) based on movement of the shaft, as described above in reference to FIGS. 1-9.

In one example, the surgical retractor 200 includes a first plurality of linking members (e.g., linking members 114, 118, 138, and 140 of FIG. 1) that are located along a second axis (e.g., second axis 116 of FIG. 1). The first plurality of linking members are configured to rotate along the second axis based on contact with the drive gear as the drive gear is rotated.

In one example, the first plurality of linking members located along the second axis comprises a first linking member (e.g., linking member 114), a second linking member (e.g., linking member 118), a third linking member (e.g., linking member 138), and a fourth linking member (e.g., linking member 140). In this example, a coupling between the first linking member and the second linking member is based on a linear movement of the first linking member from a first position along the second axis to a second position along the second axis, as shown in FIGS. 4 and 5. Continuing with this example, a coupling between the third linking member and the fourth linking member is based on a linear movement of the third linking member from a third position along the second axis to a fourth position along the second axis, as shown in FIG. 7.

In one example, the first linking member comprises a first gear (e.g., first gear 168 of FIG. 5) located along the second axis and configured to rotate based on contact with the drive gear as the drive gear is rotated. The first linking member also comprises a first locking element (e.g., locking teeth 170 of FIG. 5) associated with the first gear. Continuing with this example, the second linking member comprises a second locking element (e.g., locking teeth 172 of FIG. 5) configured to interlock with or disengage from the first locking element. In one scenario, the second locking element is configured to interlock with the first locking element based on a linear movement of the first linking member from the first position along the second axis to the second position along the second axis, as shown in FIGS. 4 and 5. In this scenario, the second locking element is configured to disengage from the first locking element based on a linear movement of the first linking member from the second position along the second axis to the first position along the second axis, as shown in FIG. 6.

In one example, the third linking member comprises a second gear (e.g., third gear 168 of FIG. 5) located along the second axis and configured to rotate based on contact with the drive gear as the drive gear is rotated. The third linking member also comprises a third locking element (e.g., locking teeth 176 of FIG. 5) associated with the second gear. Continuing with this example, the fourth linking member comprises a fourth locking element (e.g., locking teeth 178 of FIG. 5) configured to interlock with or disengage from the third locking element. In one scenario, the fourth locking element is configured to interlock with the third locking element based on a linear movement of the third linking member from the third position along the second axis to the fourth position along the second axis, as shown in FIG. 7. In this scenario, the fourth locking element is configured to disengage from the third locking element based on a linear movement of the third linking member from the fourth position along the second axis to the third position along the second axis, as shown in FIG. 8.

In one example, the surgical retractor 200 includes a first spring (e.g., spring 1004 of FIG. 10) interposed between the first linking member and the second linking member. In one example, the surgical retractor 200 also includes a second spring (e.g., spring 1004 of FIG. 10) interposed between the third linking member and the fourth linking member.

In one example, the surgical retractor 200 includes a linking member selector (e.g., linking member selector 120 of FIG. 3) configured to rotate along the first axis. The linking member selector comprises a cylindrical body (e.g., cylindrical body 124 of FIG. 3) integrally formed with a handle (e.g., handle 122 of FIG. 3). In one example, the cylindrical body includes at least one protrusion (e.g., the protrusions 128, 129, 135, 136, 137, and 139 of FIG. 3).

In one example, the at least one protrusion of the cylindrical body (is configured to exert a force on at least one linking member of the first plurality of linking members based on selection, via the handle of the linking member selector, of a position corresponding to the at least one linking member. In this example, the force on the at least one linking member causes a coupling between the at least one linking member and another linking member of the first plurality of linking members, as described above.

In a second embodiment, the surgical retractor 200 includes a first plurality of linking members (e.g., linking members 114, 118, 138, and 140 of FIG. 1) located along a second axis (e.g., second axis 116 of FIG. 1) and configured to rotate along the second axis based on contact with the drive gear as the drive gear is rotated. Continuing with this example, the surgical retractor 200 also includes a second plurality of linking members (e.g., linking members 130 and 134 of FIG. 1) located along a third axis (e.g., third axis 132 of FIG. 1) and configured to rotate along the third axis based on contact with the drive gear as the drive gear is rotated.

In one example, the first plurality of linking members located along the second axis comprises a first linking member (e.g., linking member 114), a second linking member (e.g., linking member 118), a third linking member (e.g., linking member 138), and a fourth linking member (e.g., linking member 140). In this example, the second plurality of linking members located along the third axis comprises a fifth linking member (e.g., linking member 130) and a sixth linking member (e.g., linking member 134). Continuing with this example, a coupling between the first linking member and the second linking member is based on a linear movement of the first linking member from a first position along the second axis to a second position along the second axis, as shown in FIGS. 4 and 5. In this example, a coupling between the third linking member and the fourth linking member is based on a linear movement of the third linking member from a third position along the second axis to a fourth position along the second axis, as shown in FIG. 7. In this example, a coupling between the fifth linking member and the sixth linking member is based on a linear movement of the fifth linking member from a first position along the third axis to a second position along the third axis, as shown in FIG. 6.

In one example, the first linking member comprises a first gear (e.g., first gear 168 of FIG. 5) located along the second axis (e.g., second axis 116) and configured to rotate based on contact with the drive gear as the drive gear is rotated. The first linking member also comprises a first locking element (e.g., locking teeth 170 of FIG. 5) associated with the first gear. Continuing with this example, the second linking member comprises a second locking element (e.g., locking teeth 172 of FIG. 5) configured to interlock with or disengage from the first locking element. In one scenario, the second locking element is configured to interlock with the first locking element based on a linear movement of the first linking member from the first position along the second axis to the second position along the second axis, as shown in FIGS. 4 and 5. In this scenario, the second locking element is configured to disengage from the first locking element based on a linear movement of the first linking member from the second position along the second axis to the first position along the second axis, as shown in FIG. 6.

In one example, the third linking member comprises a second gear (e.g., third gear 168 of FIG. 5) located along the second axis (e.g., second axis 116) and configured to rotate based on contact with the drive gear as the drive gear is rotated. The third linking member also comprises a third locking element (e.g., locking teeth 176 of FIG. 5) associated with the second gear. Continuing with this example, the fourth linking member comprises a fourth locking element (e.g., locking teeth 178 of FIG. 5) configured to interlock with or disengage from the third locking element. In one scenario, the fourth locking element is configured to interlock with the third locking element based on a linear movement of the third linking member from the third position along the second axis to the fourth position along the second axis, as shown in FIG. 7. In this scenario, the fourth locking element is configured to disengage from the third locking element based on a linear movement of the third linking member from the fourth position along the second axis to the third position along the second axis, as shown in FIG. 8.

In one example, the fifth linking member comprises a third gear (e.g., second gear 180 of FIG. 5) located along the third axis (e.g., third axis 132) and configured to rotate based on contact with the drive gear as the drive gear is rotated. The fifth linking member also comprises a fifth locking element (e.g., locking teeth 182 of FIG. 5) associated with the second gear. Continuing with this example, the sixth linking member comprises a sixth locking element (e.g., locking teeth 184 of FIG. 5) configured to interlock with or disengage from the fifth locking element. In one scenario, the sixth locking element is configured to interlock with the fifth locking element based on a linear movement of the fifth linking member from the first position along the third axis to the second position along the third axis, as shown in FIG. 6. In one scenario, the sixth locking element is configured to disengage from the fifth locking element based on a linear movement of the fifth linking member from the second position along the third axis to the first position along the third axis, as shown in FIG. 7.

In one example, the surgical retractor 200 includes a linking member selector (e.g., linking member selector 120 of FIG. 3) configured to rotate along the first axis (e.g., first axis 112 of FIG. 1). The linking member selector comprises a cylindrical body (e.g., cylindrical body 124 of FIG. 3) integrally formed with a handle (e.g., handle 122 of FIG. 3). The cylindrical body includes at least a first protrusion (e.g., protrusion 135 of FIG. 3) configured to exert a first force on at least one linking member of the first plurality of linking members. The first force is exerted, in part, based on a selection, via the handle of the linking member selector, of a position corresponding to the at least one linking member of the first plurality of linking members. In one scenario, the first force exerted on the at least one linking member causes a coupling between the at least one linking member of the first plurality of linking members and another linking member of the first plurality of linking members, as shown in FIGS. 4, 5, 7, and 9). The cylindrical body also includes at least a second protrusion (e.g., protrusion 137 of FIG. 3) configured to exert a second force on at least one linking member of the second plurality of linking members. The second force is exerted, in part, based on selection, via the handle of the linking member selector, of a position corresponding to the at least one linking member of the second plurality of linking members. In one scenario, the second force on the at least one linking member causes a coupling between the at least one linking member of the second plurality of linking members and another linking member of the second plurality of linking members, as shown in FIGS. 6 and 8.

In a third embodiment, the surgical retractor 200 includes a first plurality of linking members (e.g., linking members 114, 118, 138, and 140 of FIG. 1) located along a second axis (e.g., second axis 116 of FIG. 1) and configured to rotate along the second axis based on contact with the drive gear as the drive gear is rotated. Continuing with this example, the surgical retractor 200 also includes a second plurality of linking members (e.g., linking members 130, 134, 142, and 144 of FIG. 1) located along a third axis (e.g., third axis 132 of FIG. 1) and configured to rotate along the third axis based on contact with the drive gear as the drive gear is rotated.

In one example, the surgical retractor 200 includes a linking member selector (e.g., linking member selector 120 of FIG. 3) configured to rotate along the first axis (e.g., first axis 112 of FIG. 1). The linking member selector comprises a cylindrical body (e.g., cylindrical body 124 of FIG. 3) integrally formed with a handle (e.g., handle 122 of FIG. 3). The cylindrical body includes at least a first protrusion (e.g., protrusion 135 of FIG. 3) configured to exert a first force on at least one linking member of the first plurality of linking members. The first force is exerted, in part, based on a selection, via the handle of the linking member selector, of a position corresponding to the at least one linking member of the first plurality of linking members. In one scenario, the first force exerted on the at least one linking member causes a coupling between the at least one linking member of the first plurality of linking members and another linking member of the first plurality of linking members, as shown in FIGS. 4, 5, 7, and 9. The cylindrical body also includes at least a second protrusion (e.g., protrusion 137 of FIG. 3) configured to exert a second force on at least one linking member of the second plurality of linking members. The second force is exerted, in part, based on selection, via the handle of the linking member selector, of a position corresponding to the at least one linking member of the second plurality of linking members. In one scenario, the second force on the at least one linking member causes a coupling between the at least one linking member of the second plurality of linking members and another linking member of the second plurality of linking members, as shown in FIGS. 6 and 8.

Figure 14:
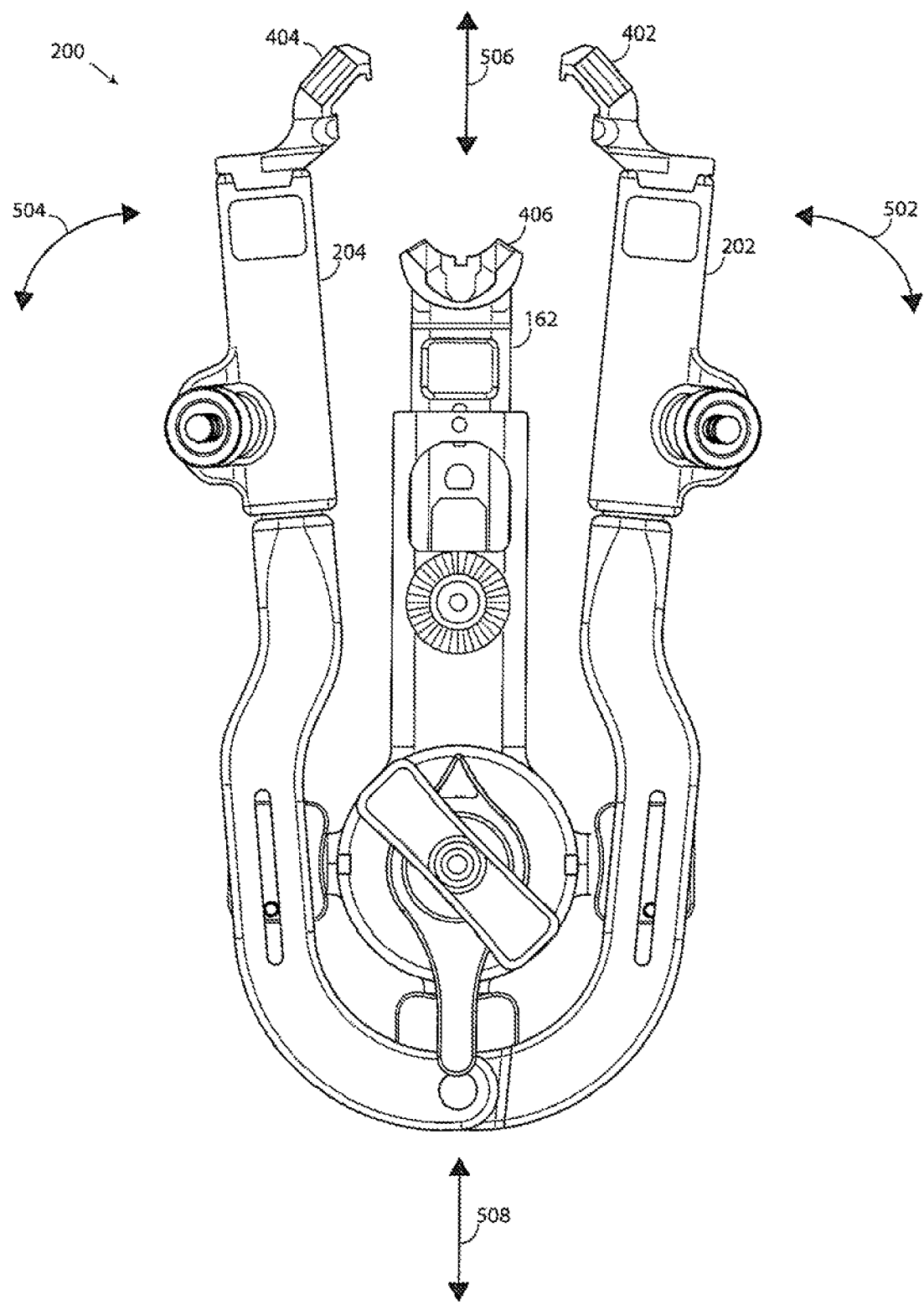
FIG. 14 illustrates a top view of the example tissue retraction system of FIG. 13, according to an embodiment of the present disclosure.

FIG. 14 illustrates a top view of the surgical retractor 200 and retractor blades 402, 404, and 406 of FIG. 13 in an open or retracted position. In one example, the right arm assembly 202 is configured to move along a trajectory 502 based on a corresponding movement of at least two linking members of the first plurality of linking members. The movement of the right arm assembly 202 along the trajectory 502 would further enable the first retractor blade 402 to move along the trajectory 502. Continuing with this example, the left arm assembly 204 is configured to move along a trajectory 504 based on a corresponding movement of at least another two linking members of the first plurality of linking members. Similarly, the movement of the left arm assembly 204 along the second trajectory 504 would further enable the second retractor blade 404 to move along the trajectory 504.

In one example, the center arm 162 is configured to move along a trajectory 506 based on a corresponding movement of at least two linking members of the second plurality of linking members. The movement of the center arm 162 along the trajectory 506 would further enable the third retractor blade 406 to move along the trajectory 506.

In one example, the right arm assembly 202 is configured to move along a trajectory 502 based on a corresponding movement of at least two linking members of the first plurality of linking members and a trajectory 508 based on a corresponding movement of at least two linking members of the second plurality of linking members. The movement of the right arm assembly 202 along the trajectory 502 would further enable the first retractor blade 402 to move along either the trajectory 502 or the trajectory 508. Continuing with this example, the left arm assembly 204 is configured to move along a trajectory 504 based on a corresponding movement of at least another two linking members of the first plurality of linking members and a trajectory 508 based on a corresponding movement of at least two linking members of the second plurality of linking members. Similarly, the movement of the left arm assembly 204 along the second trajectory 504 would further enable the second retractor blade 404 to move along either the trajectory 504 or the trajectory 508.

Figure 15:
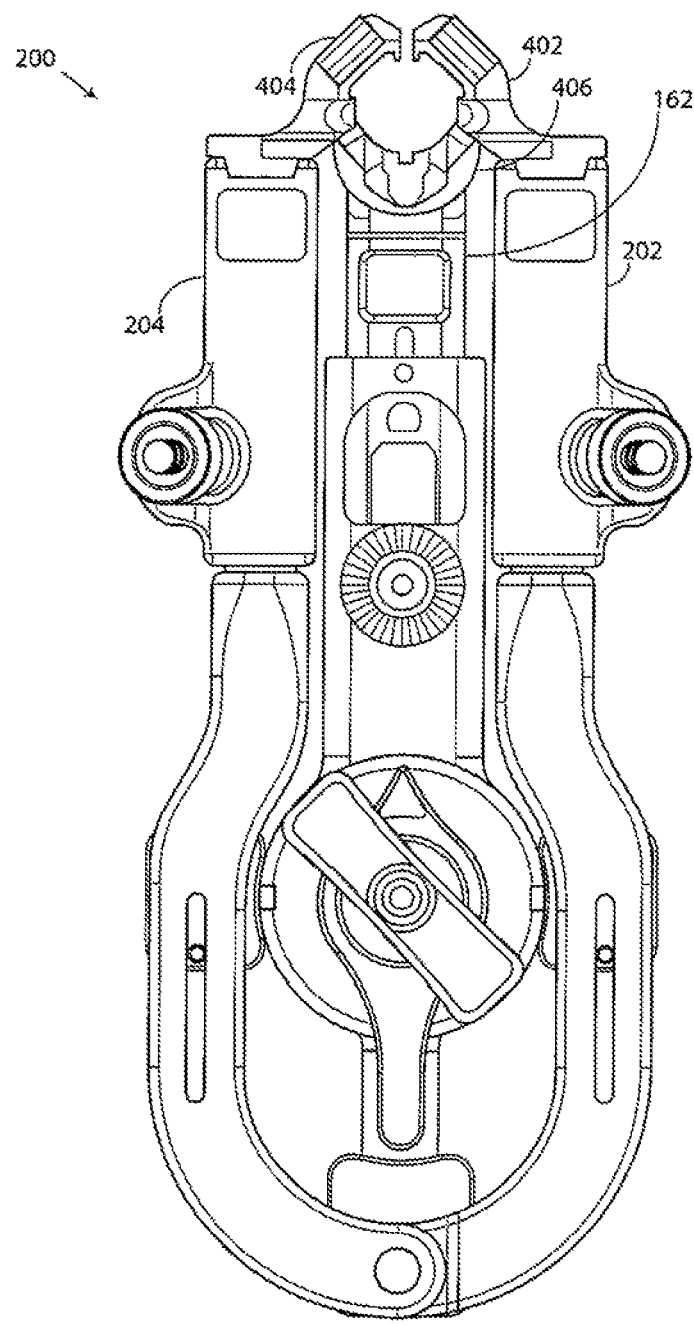
FIG. 15 illustrates a top view of an example tissue retraction system, according to an embodiment of the present disclosure.

FIG. 15 illustrates a top view of the surgical retractor 200 and retractor blades 402, 404, and 406 of FIG. 13 in a closed position. In one example, the surgical retractor 200 and retractor blades 402, 404, and 406 may be advanced, with the blades in a first generally closed position, over the exterior of an initial dilator. Once the surgical retractor 200 is in a predetermined position, a linking member selector (e.g., linking member selector 124 of FIG. 1) and a dial (e.g., dial 104 of FIG. 1) may be operated to move the retractor blades into a second, open or retracted position to create an operative corridor to the surgical target site, as shown in FIG. 14. In one scenario, the linking member selector and the dial may be rotated along a first axis (e.g., first axis 112 of FIG. 1) to enable movement of one or more of the retractor blades.

Figure 20:
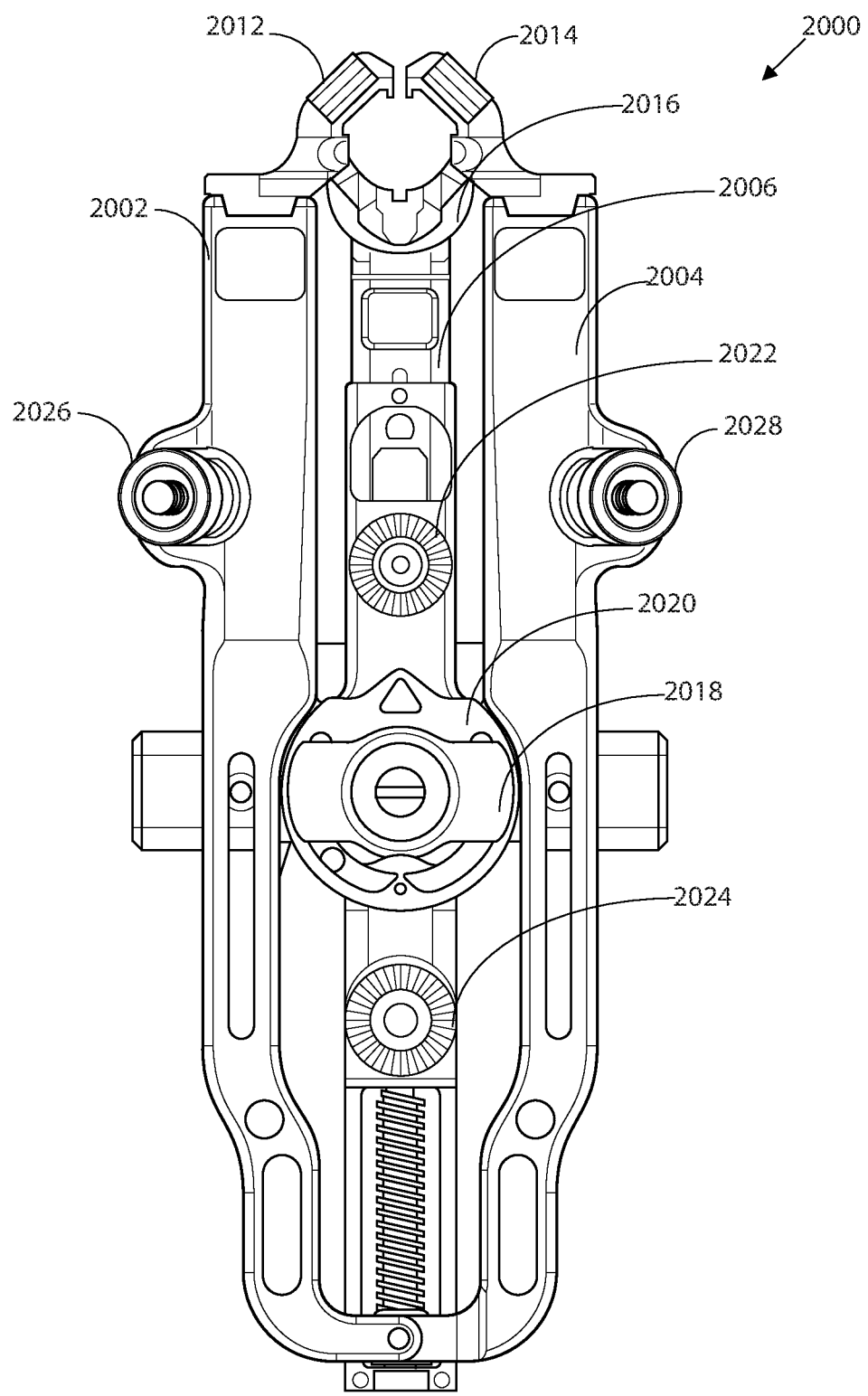
FIG. 20 illustrates a top view of another example tissue retraction system, according to an embodiment of the present disclosure.

FIG. 20 illustrates a top view of another example surgical retractor 2000. The surgical retractor 2000 comprises the assembly 100 of FIG. 1, a left arm assembly 2002, a right arm assembly 2004, and a center arm assembly 2006 and is configured to operate in a similar manner as described above with reference to the surgical retractor 200. The surgical retractor 2000 also comprises retractor blades 2012, 2014, and 2016. In one example, the surgical retractor 2000 and retractor blades 2012, 2014, and 2016 may be advanced, with the blades in a first generally closed position, over the exterior of an initial dilator (not shown). The surgical retractor 2000 also comprises a dial or handle 2008 (that is configured to operate in a similar manner to dial 104 of FIG. 1) and a selector 2020 (that is configured to operate in a similar manner to the linking member selector 124 of FIG. 1). The surgical retractor 2000 also comprises a first articulation arm attachment 2022 (that is configured to operate in a similar manner to the post 146 of FIG. 1) and a second articulating arm attachment 2024. The surgical retractor 2000 also comprises a first splay adjustment feature 2026 and a second splay adjustment feature 2028 which may be operated to adjust the angle of the first blade 2012 and second blade 2014, respectively, relative to the direction of insertion to further customize the exposure to the surgical site. According to the exemplary embodiment, the 2008 and the dial or handle may be rotated independently of each other along a first axis. Rotation of the selector to a designated position determines which blade or blades will move when the dial or handle is rotated.

The surgical retractor 2000 has a plurality of modes that dictate which retractor blades 2012, 2014 and 2016 will be actuated by rotation of the dial or handle 2018 while the selector 2020 is in a specific position. In one example, the surgical retractor 2000 is configured to operate in three modes. In this example, when the selector 2020 is in a first position, actuation of the drive gear (not shown) via the dial or handle 2018 will move retractor blade 2012 along a first trajectory. Continuing with this example, when the selector 2020 is in a second position, actuation of the drive gear will move retractor blade 2014 along a second trajectory. Still continuing with this example, when the selector 2020 is in a third position, actuation of the drive gear will move both retractor blades 2012 and 2014 along the first and second trajectories, respectively.

In another example, the surgical retractor 2000 is configured to operate in four modes. In this example, when the selector 2020 is in a first position, actuation of the drive gear via the dial or handle 2018 will move retractor blade 2012 along a first trajectory. Continuing with this example, when the selector 2020 is in a second position, actuation of the drive gear will move retractor blade 2014 along a second trajectory. Further continuing with this example, when the selector 2020 is in a third position, actuation of the drive gear will move both retractor blades 2012 and 2014 along the first and second trajectories, respectively. Continuing with this example, when the selector 2020 is in a fourth position, actuation of the drive gear will move the both retractors blades 2012 and 2014 along a third trajectory. In one scenario, the third trajectory may be perpendicular to the first and second trajectories. By way of example only, the first and second trajectories may be in the cranial/caudal direction relative to the patient and the third trajectory may be in the anterior/posterior direction relative to the patient.

In yet another example, the surgical retractor 2000 is configured to operate in five modes. In this example, when the selector 2020 is in a first position, actuation of the drive gear via the dial or handle 2018 will move retractor blade 2012 along a first trajectory. Continuing with this example, when the selector 2020 is in a second position, actuation of the drive gear will move retractor blade 2014 along a second trajectory. Continuing with this example, when the selector 2020 is in a third position, actuation of the drive gear will move both retractor blades 2012 and 2014 along the first and second trajectories, respectively. Continuing with this example, when the selector 2020 is in a fourth position, actuation of the drive gear will move the both retractor blades 2012 and 2014 along a third trajectory. Continuing with this example, when the linking member selector 2020 is in a fifth position, actuation of the drive gear will move the retractor blade 2020 along the third trajectory. By way of example only, the first and second trajectories may be in the cranial/caudal direction relative to a patient and the third and fourth trajectories may be in the anterior/posterior direction relative to the patient.

In one scenario, when closing the surgical retractor 2000 prior to removing it from a patient, both retractor blades 2012 and 2014 can be closed (i.e., moved back to their original insertion position) by turning the dial or handle 2018, even if they were moved away from their initial position by different lengths. For example, if the retractor blades 2012 and 2014 were moved unequal distances away from their initial "closed" position, when the retractor blades 2012 and 2014 are being returned to their "closed" position, the selector 2020 may be set to the mode that causes movement of both the retractor blades 2012 and 2014 along the first and second trajectories. In this example, the drive gear is actuated based on rotation of the dial or handle 2018 until both blades are in their initial closed position. The retractor blade that has the shorter distance to travel will return to its closed position first and then remain there while the retractor blade that was actuated farther away is returned to its initial closed position, without a disruption to the rotation of the dial or handle 2018. At this point, based on the retractor blade that is at a shorter distance, the interlocking teeth on a given arm assembly of either the left arm assembly 2002 or the right arm assembly 2004 would begin to ratchet, compressing a spring and then springing back repeatedly, while the other arm is continued to be pulled in based on rotation of the dial 2018. Once both the left arm assembly 2002 and the right arm assembly 2004 are in a closed position, both arm assemblies will ratchet.

In some instances, it may be desirable to pivot either the retractor blade 2012 or the retractor blade 2014 (or both) outward in order to increase the volume of the operative corridor (by increasing the distal dimension of the operative corridor). To accomplish this, the dial or handle 2018 may be removed and attached to either first or second splay adjustment mechanisms 2026 and 2028. In one example, the splay adjustment mechanism 2026, 2028 is rotated in a clockwise direction, the blade 2012, 2014 corresponding to the splay adjustment mechansim 2026, 2028 will pivot in a lateral (outward) direction. When rotating the splay adjustment mechanism 2026, 2028 in a counter-clockwise direction, the corresponding blade 2012, 2014 will pivot a lateral (inward) direction. In one example, the first or second splay adjustment mechanisms 2026 and 2028 may provide for infinite splay (i.e., the blades may be splayed to any angulation from 0° to a maximum permissible angulation).

As shown in FIG. 20, the articulating arm attachment 2024 includes a quick align feature for preliminary engagement of a "poker chip" style connector. This feature provides a user with the means to properly and securely align the teeth (i.e., peaks and valleys) of the poker chip for intersection single handedly. This feature avoids locking the poker chips together before their teeth are properly aligned. This can happen when the teeth become worn and it is more difficult to align the peeks of one poker chip in the valleys of the other poker chip.

By way of example, the retractor blades may be composed of any material suitable for introduction into the human body, including but not limited to stainless steel, aluminum, titanium, and/or clear polycarbonate, that would ensure rigidity during tissue retraction. The retractor blades may be optionally coated with a carbon fiber reinforced coating to increase strength and durability. The blades may be optionally constructed from partially or wholly radiolucent materials (e.g., aluminum, PEEK, carbon-fiber, and titanium) to improve the visibility of the surgeon during imaging (e.g., radiographic, Mill, Conn., fluoroscope, etc.). The retractor blades may also be composed of a material that would destruct when autoclaved (such as polymer containing a portion of glass particles), which may be advantageous in preventing the unauthorized re-use of the blades (which would be provided to the user in a sterile state). The retractor blades may be provided in any number of suitable lengths, depending upon the anatomical environment and surgical approach, such as (by way of example only) the range from 20 mm to 150 mm. Based on this range of sizes, the assembly 100 of FIG. 1 is extremely versatile and may be employed in any of a variety of desired surgical approaches, including but not limited to lateral, posterior, postero-lateral, anterior, and antero-lateral, by simply selecting the desired size retractor blades and attaching them to the surgical retractor 200.

In one example, the retractor blades may be equipped with various additional features or components. By way of example only, one or more of the retractor blades may be equipped with a retractor extender, such as a wide retractor extender or a narrow retractor extender. The retractor extenders extend from the retractor blades to form a protective barrier to prevent the ingress or egress of instruments or biological structures (e.g., nerves, vasculature, organs, etc. . . ) into or out of an operative corridor. Depending upon the anatomical setting and surgical approach, one or more of the retractor blades may be equipped with a shim element. In one example, the shim element has a distal tapered region which may be advanced into tissue (e.g. bone, soft tissue, etc.) for the purpose of anchoring the retractor blades and/or advanced into a disc space to distract the adjacent vertebral bodies (thereby restoring disc height). In similar fashion to the retractor extenders, the shim element also forms a protective barrier to prevent the ingress or egress of instruments or biological structures (e.g., nerves, vasculature, etc.) into or out of the operative corridor.

In one example, the retractor extenders and/or the shim element may be made out any material suitable for use in the human body, including but not limited to biologically compatible plastic and/or metal, preferably partially or wholly radiolucent in nature material (such as aluminum, PEEK, carbon-fibers and titanium). Construction from plastic or thin metal provides the additional benefit of allowing the shim and/or the retractor extenders to be collapsed into a compressed or low profile configuration at the skin level as the element is inserted, and then expanded once it is below skin level and within the operative corridor. In another example, the retractor extenders may have symmetric narrow configurations and/or broad configurations and/or an asymmetric configuration of narrow and broad elements. For example, any or all of the retractor extenders may be provided with a lateral section, a narrow configuration, and/or a lateral section. The retractor extenders and/or the shim element may be composed of a material that would destruct when autoclaved (such as polymer containing a portion of glass particles), which may be advantageous in preventing the unauthorized re-use of the retractor extenders and/or the shim element (which would be provided to the user in a sterile state). Slits may also be provided on the shim to improve flexibility. The retractor extenders and/or the shim element may have a parabolic concave curvature.

In one example, each of the retractor extenders and/or the shim element may be equipped with a mechanism to selectively and releasably engage with the respective retractor blades. By way of example only, this may be accomplished by configuring the retractor extenders and/or the shim element with a tab element capable of engaging with corresponding ratchet-like grooves along the inner-facing surfaces of the retractor blades. Each of the retractor extenders and/or the shim element is provided with a pair of engagement elements having, by way of example only, a generally dove-tailed cross-sectional shape. The engagement elements are dimensioned to engage with receiving portions on the respective retractor blades. In a preferred embodiment, each of the retractor extenders and/or the shim element may be provided with an elongate slot for engagement with an insertion tool. Each tab member is also equipped with an enlarged tooth element which engages within corresponding grooves provided along the inner surface of the retractor blades. On the wide retractor extenders, each includes a center portion flanked by a pair of lateral sections, which effectively increase the width of the retractor blades.

In another example, any or all of the retractor blades, the retractor extenders, and/or the shim element may be provided with one or more electrodes (preferably at or near their distal regions) equipped for use with a nerve surveillance system, such as, by way of example, the type shown and described in Int'l Patent App. Ser. Nos. PCT/US02/30617 filed on Sep. 25, 2002, filed on Jul. 11, 2002, Intl Patent App. Ser. No. PCT/US2008/004427, filed Apr. 3, 2008 ("Neurophysiology Monitoring Patents") the entire contents of which are each expressly incorporated by reference herein. Such a nerve surveillance system is capable of detecting the existence of (and optionally the distance and/or direction to) neural structures during the retraction of tissue by detecting the presence of nerves by applying a stimulation signal to electrodes and monitoring the evoked EMG signals from the myotomes associated with the nerves in the vicinity of the retractor blades. In so doing, the system as a whole (including the surgical retractor 200) may be used to form an operative corridor through (or near) any of a variety of tissues having such neural structures, particularly those which, if contacted or impinged, may otherwise result in neural impairment for the patient. In this fashion, the access system of the surgical retractor 200 may be used to traverse tissue that would ordinarily be deemed unsafe or undesirable, thereby broadening the number of manners in which a given surgical target site may be accessed.

Figure 16:
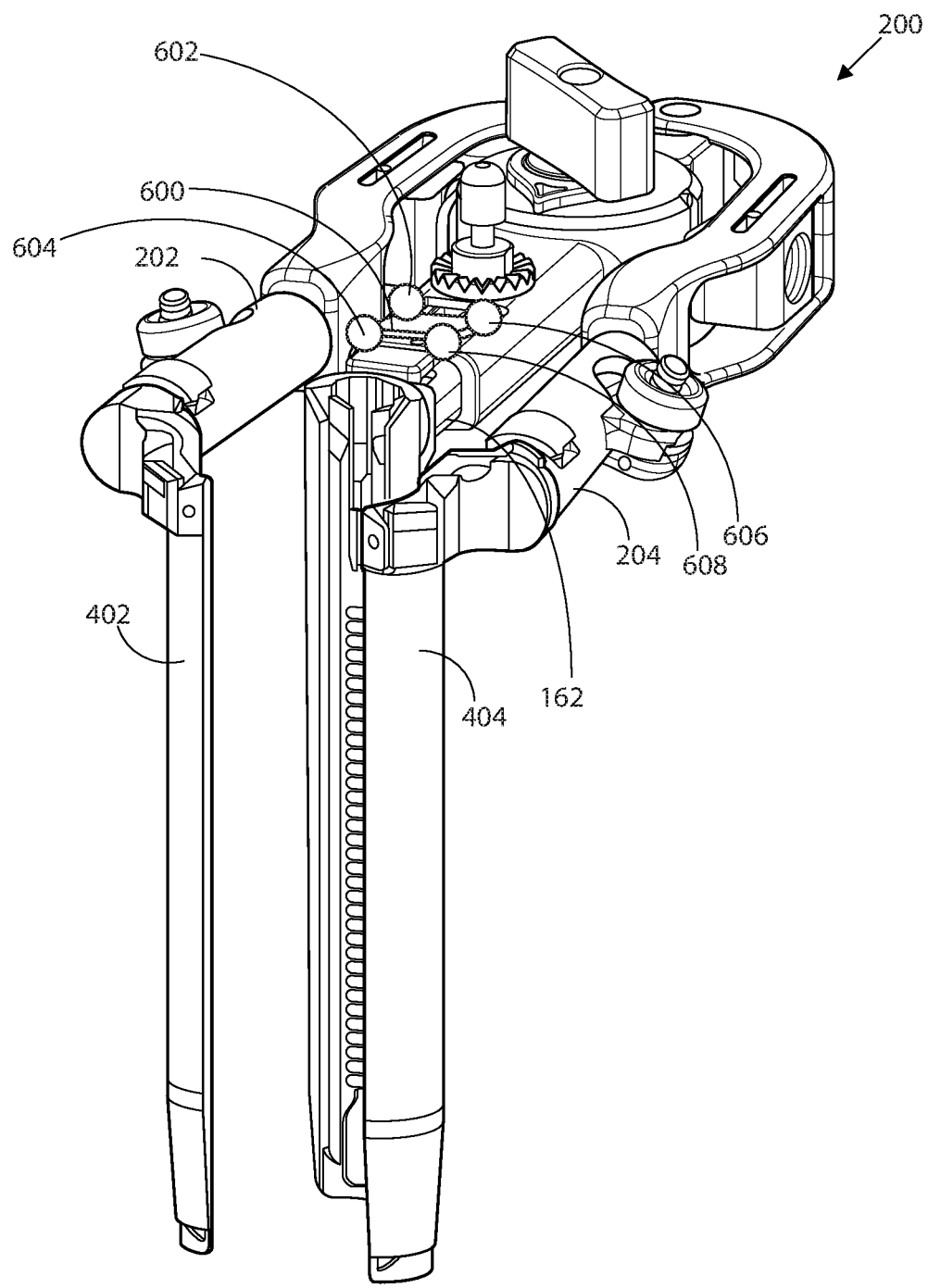
FIG. 16 illustrates an example tissue retraction system, according to an embodiment of the present disclosure.

FIG. 16 illustrates the example surgical retractor 200 with retractor blades 402, 404, and 406 in an open position and an array 600. As described above, the example surgical retractor 200 comprises the assembly 100 of FIG. 1. The array 600 includes tracking markers 602, 604, 606, and 608. Although only four spherical tracking markers are shown in FIG. 16, it is envisioned that more or less tracking markers could be utilized. In one example, the tracking markers are hemispherical. In another example, the array is configured to include tracking markers in six degrees of freedom. In one example, the array is a 360 degree array. The array 600 is releasably secured to the center arm 162. In one example, the array 600 enables a navigation system to track the location or position of the surgical retractor 200 during a surgical procedure.

As described herein, the term "navigation" describes the ability to leverage intraoperative imaging in real-time to obtain spatial awareness between anatomical structures and instrumentation. A navigation system provides maximum surgeon visualization with minimal radiation exposure through an innovative and efficient solution during minimally invasive surgery (MIS) and traditional open spine procedures. For example, a navigation system enables surgeons to perform three-dimensional (3D) image-guided surgery with increased accuracy exposure during posterior and anterior column procedures. This provides benefits for surgeons and hospitals alike: 1) for degenerative and MIS surgeons who desire improved visualization while simultaneously reducing radiation exposure; 2) for deformity surgeons who desire real-time spinopelvic parameter assessment and anatomical orientation in complex spine procedures; and 3) for hospital administrators who desire to reduce the total cost of health care through more predictable outcomes form accurate implant placement and reduced morbidity of MIS procedures.

The navigation system described herein is compatible with spine procedures and the instruments and implants associated therewith. By way of example, the navigation system described herein is also compatible with open and MIS pedicle screw placements for thoracolumbar fusions, lateral interbody fusion procedures including lateral lumbar interbody fusion (XLIF), trauma procedures, maximum access surgery transforaminal lumbar interbody fusion (MAS TLIF), maximum access surgery posterior lumbar interbody fusion (MAS PLIF), lateral fixation procedures, corpectomies, anterior cervical discectomy and fusion (ACDF), and posterior cervical fusion (PCF). It is contemplated that the navigation system will integrate planning, such as the iGA platform by NuVasive, Inc., intraoperative monitoring, automated rod bending, etc. to provide a holistic view of the anatomy and foster enhanced procedural solutions.

Figure 17:
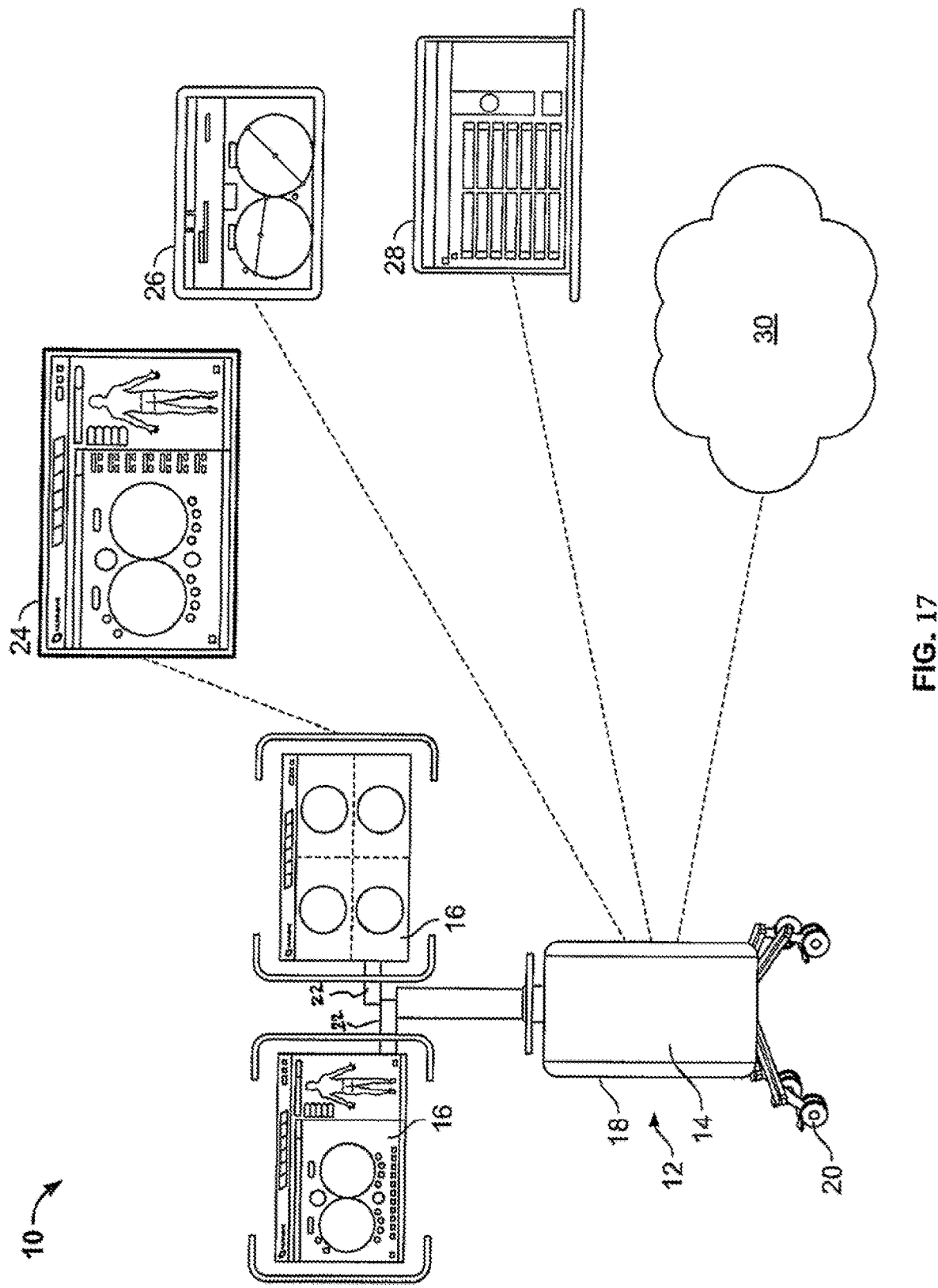
FIG. 17 illustrates an example computing system, according to an embodiment of the present disclosure.

FIG. 17 illustrates an example navigation system 10 that may be used to track instruments, such as a surgical retractor. As shown in FIG. 17, the navigation system 10 may include one or more hardware components, one or more software components, and one or more auxiliary components. For example, the navigation system 10 may include a computing system 12 including a control unit 14 including at least one processor configured to execute computer executable instructions (i.e., software), and one or more display screens 16. The control unit 14 may be housed in a technology hub 18 having one or more locking wheels 20 disposed thereon such that the technology hub 18 may be easily positionable around an operating room (OR). The technology hub 18 may include one or more arms 22 connecting to the display screens 16. The control unit 14 may be configured for executing the application software and algorithms, and communicating and interfacing with other system components associated with the navigation system 10, such as auxiliary displays 24, remote control devices 26, such as tablets or phones, and mobile computing devices 28, such as intraoperative neuromonitoring technician laptops, and cloud remote and cloud planning systems 30.

The computing system 12 may receive universal imaging inputs, meaning that it has the ability to work with a pre-operative computerized tomography (CT) input, a pre-operative magnetic resonance imaging (MRI) input, a 3D C-arm input, or an intraoperative CT input. The imaging inputs may be formatted according to industry standards, such as the Digital Imaging and Communications in Medicine (DICOM) standard, the Picture Archive and Communication System (PACS) standard, Phase Alternating Line (PAL) standard, and National Television System Committee (NTSC) standard. The system 12 may receive the input over one or more networks (e.g., wired or wireless local area network, such as a hospital PACS) or via USB, CD, DVD, DVI, composite video, or analog video. Advantageously, as discussed herein, the present system 10 employs automatic registration with intra-operative and pre-op CT images, the system 10 is configured to perform segmentation of each vertebral body through image recognition, and the system 10 is configured to register individual vertebral bodies such that the spine can be dynamically tracked during the surgical procedure.

The one or more display screens 16 may be touch screens such that they include a graphical user interface (GUI) with which the user can directly input commands by touching the screen 16. The system 10 offers intuitive and convenient system interaction with the software and hardware available to surgeons (and users others within the surgical field) and other hospital personnel (outside the surgical field). While various descriptions of the aspects of the present disclosure may refer to a surgeon, or surgeons, it is to be understood that the functionality of such aspects may extend to other users, as contextually appropriate, such that the term "surgeon(s)" supports the term "user(s)." The software may be primarily controlled through the touch screen graphical user interface on the one or more display screens 16, which controls the navigation system 10. In one embodiment, the system 10 includes a secondary control through the one or more remote control devices 26.

The navigation system 10 receives data and inputs from various other parts of the system 10, including the 3D imaging data and optical camera(s) 34, 36 that track surgical instruments (e.g., surgical retractor 200 of FIG. 16), surgeon inputs, and processing to provide real-time navigation information to the surgeon or OR personnel. The surgeon/OR personnel can interact with the navigation software from the sterile field for navigation view settings, instrument selection/calibration real-time implant planning and sizing, administrative features, and option selection. The software is controlled without interfering with other intraoperative computer-assisted modalities and the system 10 is able to easily transition between navigation modes and other modes, for example, intraoperative neuromonitoring (TOM) services, NUVAMAP O.R., and BENDINI software modes.

Figure 18:
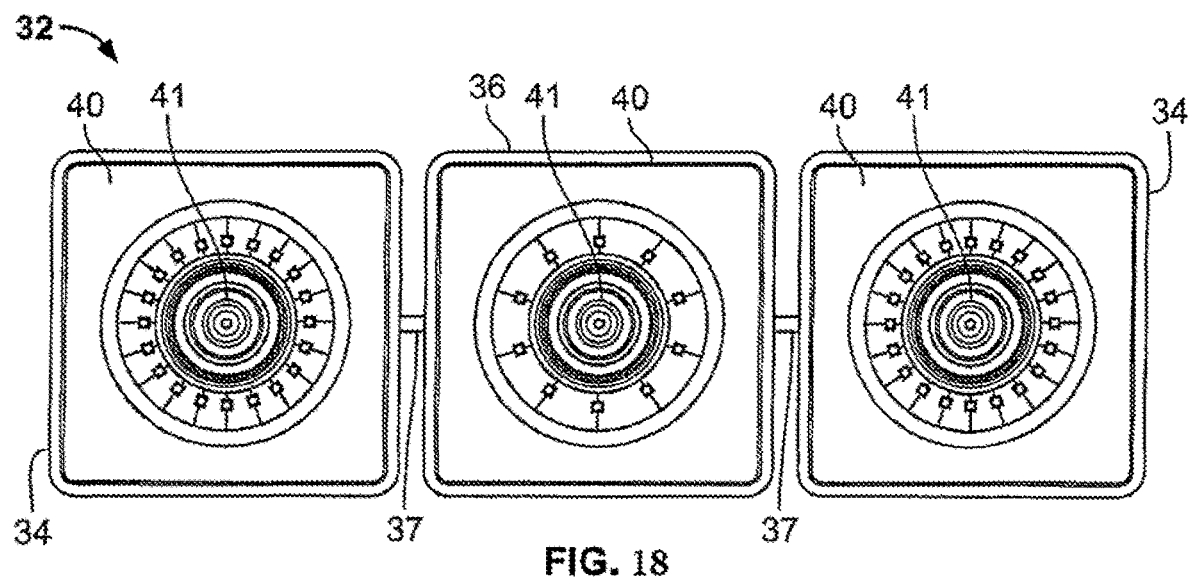
FIG. 18 illustrates an example optical tracking system, according to an embodiment of the present disclosure.
Figure 19:
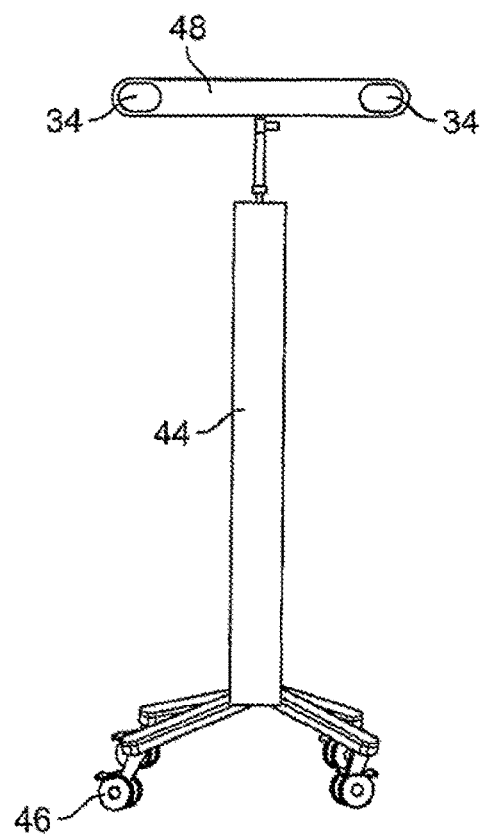
FIG. 19 illustrates an example optical tracking system and a mobile card, according to an embodiment of the present disclosure.

In another example of the navigation system 10, the system 10 includes an optical tracking system 32, as shown in FIGS. 18 and 19. The optical tracking system 32 may provide real-time location of objects (e.g., one or more instruments for use in surgery) in relationship to each other as the objects move through space. The optical tracking system 32 may be in communication with the control unit 14 of the computing system 12 of the navigation system 10. The optical tracking system 32 may include one or more cameras that are infrared (IR) cameras 34 and/or visible light cameras 36 (i.e., sense and transmit data from the IR or visible light spectrums). Each camera 34 and 36 may be selected between IR and visible light modes under software control by the control unit 14. The optical tracking system 32 senses (i.e., sees) the location of one or more tracking arrays within the field of view of the system 32. The tracking arrays may be positioned on one or more surgical instruments. The optical tracking system 32 provides the navigation system 10 with dynamic 3D position information corresponding to the anatomical the surgical instruments being tracked.

The optical tracking system 32 may be configured in any suitable orientation. In one embodiment, illustrated in FIG. 18, the optical tracking system 32 includes a first and a second IR camera 34 flanking a first visible light camera 36. The cameras 34, 36 may be discrete units or connected together by a camera base 37. The cameras 34, 36 may be compact enough to be positioned within a sterile field of a surgical procedure without interfering with the procedure. The cameras 34, 36 may contain a high number of pixels. As used herein, the term, "pixel" is used to refer to a single scalar element of a multi-component representation (also referred to as a photosite). The cameras 34, 36 may capture at least 1 megapixel, at least 2 megapixels, at least 5 megapixels, at least 10 megapixels, at least 12 megapixels, at least 15 megapixels, or at least 20 megapixels. A thin, transparent barrier 40 may be placed over the lenses 41 of the cameras 34, 36. Advantageously, a high pixel count enables the barrier 40 to be placed over the lenses 41 of the cameras 34, 36 while the cameras 34, 36 are in-use without sacrificing the accuracy of the position of the sensed tracking arrays 38. The barrier 40 also enables the cameras 34, 36 to be draped and placed within the sterile field. Another benefit of embodiments of the system 10 having the barrier 40 is that the barrier 40 enables the cameras 34, 36 to be in close proximity with the tracking arrays 38, which further allows the arrays 38 to be reduced in dimensions such that the arrays 38 are less likely to interfere with the surgical procedure being performed.

The optical tracking system 32 may be used with markers 42 disposed on one or more arrays (discussed below). The markers 42 may be small in size (e.g., 3 mm diameter or as small as technologically feasible) with a minimal tracking array footprint. In addition to tracking spatially track arrays, the optical tracking system 32 may track objects that have arrays as the objects change orientation (e.g., rotation, yaw, roll). The optical tracking system 32 may be positioned within the OR to minimize the potential for line-of-sight disruptions with a subject for the surgeon performing the surgical procedure.

In embodiments of the navigation system 10 where the cameras 34, 36 are placed outside of the sterile field, the cameras 34, 36 may be placed on a mobile cart 44 (FIG. 19) with one or more locking wheels 46 such that the cart 44 may be positioned variously by rolling the cart 44 within the OR. The cart 44 may be placed proximate to one end of a surgical bed. The cart 44 may comprise a base 48 for receiving the cameras 34, 36. The base 48 may be lockingly adjustable, including height, longitudinally, and laterally so that the cameras 34, 36 may be optimally positioned for the surgical procedure.

In embodiments of the navigation system 10 where the cameras 34, 36 are placed within the sterile field, the draped cameras 34, 36 may be configured to view the C-arm 194, arrays 38 (including on instruments) by placing one or more cameras 34, 36 at one of the following locations: patient anchor attachment, bedrail attachment, cart attachment, an overhead boom/light attachment, or any combination thereof. Some embodiments of the navigation system 10, discussed below, include the optical tracking system 32 that allows a single (i.e., initial) set up of the cameras 34, 36 with no additional adjustments necessary or made during a surgical procedure, thereby improving surgical workflow efficiency by eliminating the need for hospital personnel to adjust and re-adjust the cameras 34, 36 during the operative procedure to "see" or calibrate the navigated instruments 6 or the markers 42.

In one embodiment, the navigation system 10 of FIG. 17 includes computer executable instructions containing instructions to track and correlate the real time location of surgical retractor 200. In one example, the computer executable instructions are configured to display a simulation of the surgical retractor 200 overlaid onto an image of a surgical site on a display screen (e.g., display screens 16 of FIG. 16). In one example, the computer system 12 of FIG. 16 is in communication with the touch screen display 16, which can display data from the system 10 to the surgeon and receive input data from the system. The computer system 12 is in communication with the optical tracking system 32, including the IR cameras 34 and the visible light cameras 36. The computer system 12 may control the cameras 34, 36 (views, IR/visible light functionality, etc.), cause the cameras 34, 36 to capture and transmit images, and receive image data from the cameras 34, 36.

Any of the features or attributes of the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. A tissue retraction system comprising:
   a drive gear coupled to a shaft, wherein the drive gear is configured to rotate along a first axis based on movement of the shaft;
   a first plurality of linking members located along a second axis and configured to rotate along the second axis based on contact with the drive gear as the drive gear is rotated;
   a second plurality of linking members located along a third axis and configured to rotate along the third axis based on contact with the drive gear as the drive gear is rotated;
   a linking member selector configured to rotate along the first axis, wherein the linking member selector comprises a cylindrical body integrally formed with a handle, wherein the cylindrical body includes at least a first protrusion configured to exert a first force on at least one linking member of the first plurality of linking members based on selection, via the handle of the linking member selector, of a position corresponding to the at least one linking member of the first plurality of linking members, wherein the cylindrical body includes at least a second protrusion configured to exert a second force on at least one linking member of the second plurality of linking members based on selection, via the handle of the linking member selector, of a position corresponding to the at least one linking member of the second plurality of linking members;
   a right arm assembly configured to move along a first trajectory based on a corresponding movement of at least two linking members of the first plurality of linking members;
   a first retractor blade coupled to the right arm assembly;
   a left arm assembly configured to move along a second trajectory based on a corresponding movement of at least another two linking members of the first plurality of linking members;
   a second retractor blade coupled to the left arm assembly;
   a center arm configured to move along a third trajectory based on a corresponding movement of at least two linking members of the second plurality of linking members;
   a third retractor blade coupled to the center arm; and
   an array including tracking markers, wherein the array is releasably secured to the center arm.

2. The system of claim 1, wherein the system is configured such that:
   the first force on the at least one linking member causes a coupling between the at least one linking member of the first plurality of linking members and another linking member of the first plurality of linking members; and
   the second force on the at least one linking member causes a coupling between the at least one linking member of the second plurality of linking members and another linking member of the second plurality of linking members.

3. The system of claim 1, wherein the system further comprises:
   a post located along a fourth axis parallel and offset to the first axis; and
   locking teeth secured to the system at a first end of the post, where in the post includes at least one tapered surface.

4. The system of claim 3, wherein the system further comprises:
   an articulating arm connector that includes:
      an aperture;
      a button with a tapered surface; and
      locking teeth,
   wherein the aperture is configured to receive the post; and
   wherein the tapered surface of the button is configured to interface with the at least one tapered surface of the post, wherein the locking teeth of the post are configured to engage with the locking teeth secured to the system.

5. The system of claim 1,
wherein the first plurality of linking members located along the second axis comprises a first linking member, a second linking member, a third linking member, and a fourth linking member;
wherein a coupling between the first linking member and the second linking member is based on a linear movement of the first linking member from a first position along the second axis to a second position along the second axis;
wherein a coupling between the third linking member and the fourth linking member is based on a linear movement of the third linking member from a third position along the second axis to a fourth position along the second axis;
wherein the second plurality of linking members located along the third axis comprises a fifth linking member and a sixth linking member; and
wherein a coupling between the fifth linking member and the sixth linking member is based on a linear movement of the fifth linking member from a first position along the third axis to a second position along the third axis.

6. The system of claim 1, wherein the markers are hemispherical.

7. The system of claim 1, wherein the array includes markers in six degrees of freedom.

8. The system of claim 1, wherein the array is a 360-degree array.

9. A system comprising:
a surgical retractor that includes:
a drive gear coupled to a shaft, wherein the drive gear is configured to rotate along a first axis based on movement of the shaft;
a first plurality of linking members located along a second axis and configured to rotate along the second axis based on contact with the drive gear as the drive gear is rotated;
a second plurality of linking members located along a third axis and configured to rotate along the third axis based on contact with the drive gear as the drive gear is rotated;
a linking member selector configured to rotate along the first axis, wherein the linking member selector comprises a cylindrical body integrally formed with a handle,
wherein the cylindrical body includes at least a first protrusion configured to exert a first force on at least one linking member of the first plurality of linking members based on selection, via the handle of the linking member selector, of a position corresponding to the at least one linking member of the first plurality of linking members, wherein the cylindrical body includes at least a second protrusion configured to exert a second force on at least one linking member of the second plurality of linking members based on selection, via the handle of the linking member selector, of a position corresponding to the at least one linking member of the second plurality of linking members;
a right arm assembly configured to move along a first trajectory based on a corresponding movement of at least two linking members of the first plurality of linking members;
a first retractor blade coupled to the right arm assembly;
a left arm assembly configured to move along a second trajectory based on a corresponding movement of at least another two linking members of the first plurality of linking members;
a second retractor blade coupled to the left arm assembly;
a center arm configured to move along a third trajectory based on a corresponding movement of at least two linking members of the second plurality of linking members;
a third retractor blade coupled to the center arm; and
an array including tracking markers, wherein the array is releasably secured to the center arm; and
at least one camera configured to track the array and transmit one or more images of the array to a computing system including a processor, wherein the computing system is configured to display a simulation of the surgical retractor on a display screen.

10. The system of claim 9, wherein the system is configured such that:
the first force on the at least one linking member causes a coupling between the at least one linking member of the first plurality of linking members and another linking member of the first plurality of linking members; and
the second force on the at least one linking member causes a coupling between the at least one linking member of the second plurality of linking members and another linking member of the second plurality of linking members.

11. The system of claim 9, wherein the system further comprises:
a post located along a fourth axis parallel and offset to the first axis; and
locking teeth secured to the system at a first end of the post, where in the post includes at least one tapered surface.

12. The system of claim 11, wherein the system further comprises:
an articulating arm connector that includes:
an aperture;
a button with a tapered surface; and
locking teeth,
wherein the aperture is configured to receive the post;
wherein the tapered surface of the button is configured to interface with the at least one tapered surface of the post; and
wherein the locking teeth of the post are configured to engage with the locking teeth secured to the system.

13. The system of claim 9,
wherein the first plurality of linking members located along the second axis comprises a first linking member, a second linking member, a third linking member, and a fourth linking member;
wherein a coupling between the first linking member and the second linking member is based on a linear movement of the first linking member from a first position along the second axis to a second position along the second axis;
wherein a coupling between the third linking member and the fourth linking member is based on a linear movement of the third linking member from a third position along the second axis to a fourth position along the second axis;
wherein the second plurality of linking members located along the third axis comprises a fifth linking member and a sixth linking member; and
wherein a coupling between the fifth linking member and the sixth linking member is based on a linear movement of the fifth linking member from a first position along the third axis to a second position along the third axis.

14. The system of claim 9, wherein the markers are hemispherical.

15. The system of claim 9, wherein the array includes markers in six degrees of freedom.

16. The system of claim 9, wherein the array is a 360-degree array.

17. A system comprising:
a surgical retractor that includes:
  a drive gear coupled to a shaft, wherein the drive gear is configured to rotate along a first axis based on movement of the shaft;
  a first plurality of linking members located along a second axis and configured to rotate along the second axis based on contact with the drive gear as the drive gear is rotated;
  a second plurality of linking members located along a third axis and configured to rotate along the second axis based on contact with the drive gear as the drive gear is rotated;
  a linking member selector configured to rotate along the first axis, the linking member selector comprising a cylindrical body integrally formed with a handle, wherein the cylindrical body includes at least a first protrusion configured to exert a first force on at least one linking member of the first plurality of linking members based on selection, via the handle of the linking member selector, of a position corresponding to the at least one linking member of the first plurality of linking members, wherein the first force on the at least one linking member causes a coupling between the at least one linking member of the first plurality of linking members and another linking member of the first plurality of linking members, wherein the cylindrical body includes at least a second protrusion configured to exert a second force on at least one linking member of the second plurality of linking members based on selection, via a handle of the linking member selector, of a position corresponding to the at least one linking member of the second plurality of linking members, wherein the second force on the at least one linking member causes a coupling between the at least one linking member of the second plurality of linking members and another linking member of the second plurality of linking members;
  a right arm assembly configured to move along either a first trajectory or a second trajectory, wherein the first trajectory corresponds to a movement of at least two linking members of the first plurality of linking members, wherein the second trajectory corresponds to a movement of at least two linking members of the second plurality of linking members;
  a first retractor blade coupled to the right arm assembly;
  a left arm assembly configured to move along either the second trajectory or a third trajectory, wherein the third trajectory corresponds to a movement of at least two other linking members of the first plurality of linking members;
  a second retractor blade coupled to the left arm assembly;
  a center arm configured to move along a fourth trajectory based on a corresponding movement of at least two other linking members of the second plurality of linking members;
  a third retractor blade coupled to the center arm;
  a post located along a fourth axis parallel and offset to the first axis; and
  locking teeth secured to the system at a first end of the post, wherein the post includes at least one tapered surface; and
an articulating arm connector that includes:
  an aperture;
  a button with a tapered surface; and
  locking teeth, wherein the aperture is configured to receive the post, wherein the tapered surface of the button is configured to interface with the at least one tapered surface of the post, wherein the locking teeth of the post are configured to engage with the locking teeth secured to the system.

18. The system of claim 17, further comprising:
an array coupled to the surgical retractor;
a display screen;
a computing system including one or more processors configured to display a simulation of the surgical retractor on the display screen; and
at least one camera configured to track the array and transmit one or more images of the array to the computing system.

19. The system of claim 18, wherein the array inludes hemispherical markers.

20. The system of claim 18, wherein the array includes markers in six degrees of freedom.

* * * * *